United States Patent
Greenhalgh et al.

(10) Patent No.: US 9,681,889 B1
(45) Date of Patent: Jun. 20, 2017

(54) DEPTH CONTROLLED NEEDLE ASSEMBLY

(71) Applicant: SURGICAL DEVICE EXCHANGE, LLC, Boca Raton, FL (US)

(72) Inventors: Travis Greenhalgh, Boca Raton, FL (US); Ryan Lewis, Waxhaw, NC (US)

(73) Assignee: SurGenTec, LLC, Boca Raton, FL (US)

( * ) Notice: Subject to any disclaimer, the term of this patent is extended or adjusted under 35 U.S.C. 154(b) by 0 days.

(21) Appl. No.: 14/734,988

(22) Filed: Jun. 9, 2015

(51) Int. Cl.
*A61B 17/34* (2006.01)

(52) U.S. Cl.
CPC ...... *A61B 17/3421* (2013.01); *A61B 17/3472* (2013.01); *A61B 2017/3443* (2013.01)

(58) Field of Classification Search
CPC . A61B 17/3421; A61B 17/3472; A61B 17/34; A61B 17/3401; A61B 17/347; A61B 17/0469; A61B 17/0482; A61B 2017/3443; A61M 5/178; A61M 5/20
See application file for complete search history.

(56) References Cited

U.S. PATENT DOCUMENTS

| | | | |
|---|---|---|---|
| 5,250,054 A * | 10/1993 | Li | 606/148 |
| 5,368,046 A * | 11/1994 | Scarfone | A61B 10/025 600/567 |
| 5,480,389 A * | 1/1996 | McWha et al. | 604/165.02 |
| 6,019,776 A * | 2/2000 | Preissman et al. | 606/185 |
| 6,066,146 A * | 5/2000 | Carroll et al. | 606/148 |
| 6,197,002 B1 * | 3/2001 | Peterson | 604/164.01 |
| 7,643,884 B2 | 1/2010 | Pond, Jr. et al. | |
| 7,657,308 B2 | 2/2010 | Miles et al. | |
| 7,942,826 B1 | 5/2011 | Scholl et al. | |
| 7,963,927 B2 | 6/2011 | Kelleher et al. | |
| 7,976,498 B2 | 7/2011 | Swisher et al. | |
| 8,062,259 B2 | 11/2011 | Nycz et al. | |
| 8,162,889 B2 | 4/2012 | Swisher et al. | |
| 8,192,443 B2 | 6/2012 | Perez-Cruet | |
| 8,255,044 B2 | 8/2012 | Miles et al. | |
| 8,784,330 B1 | 7/2014 | Scholl et al. | |
| 2002/0022847 A1 * | 2/2002 | Ray, III | A61B 17/025 606/96 |
| 2004/0068264 A1 * | 4/2004 | Treace | 606/86 |
| 2005/0038465 A1 * | 2/2005 | Shraga | A61B 5/1411 606/182 |
| 2007/0260255 A1 * | 11/2007 | Haddock | A61B 17/3421 606/80 |
| 2008/0200915 A1 * | 8/2008 | Globerman | A61B 17/1637 606/80 |
| 2009/0024056 A1 * | 1/2009 | Bacon et al. | 600/567 |
| 2011/0093024 A1 * | 4/2011 | Layne et al. | 606/86 R |
| 2012/0226301 A1 | 9/2012 | Geist | |
| 2012/0239050 A1 * | 9/2012 | Linderman et al. | 606/94 |
| 2013/0150752 A1 * | 6/2013 | Swann | A61B 10/025 600/567 |

(Continued)

*Primary Examiner* — Alexander Orkin
(74) *Attorney, Agent, or Firm* — Knobbe Martens Olson & Bear LLP

(57) ABSTRACT

A target needle assembly can include a needle having a sharp tip, a cannula configured to receive the needle, and an outer sheath. The outer sheath is configured to receive the cannula. The target needle assembly includes a depth stop mechanism, and the outer sheath is configured to limit or inhibit further advancement of the needle into the bone once the needle has been advanced the desired distance to a target location.

9 Claims, 21 Drawing Sheets

(56) References Cited

U.S. PATENT DOCUMENTS

2014/0171946 A1* 6/2014 Benson .............. A61B 17/1655
606/79
2014/0257356 A1* 9/2014 Pacak ................ A61B 17/3417
606/185

* cited by examiner

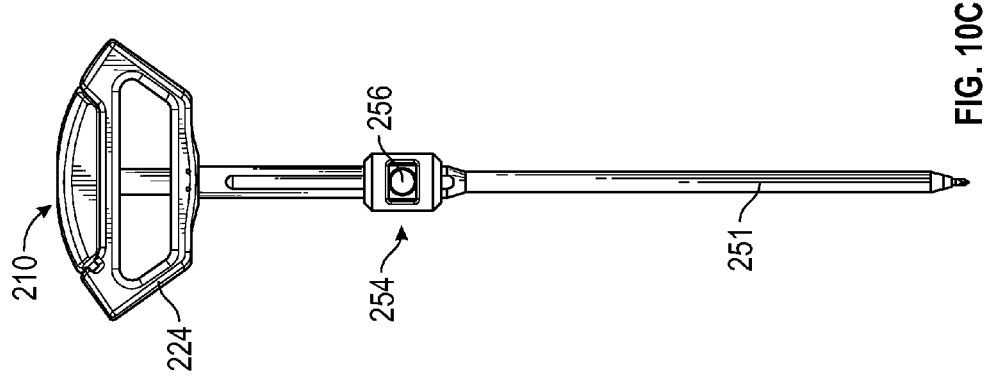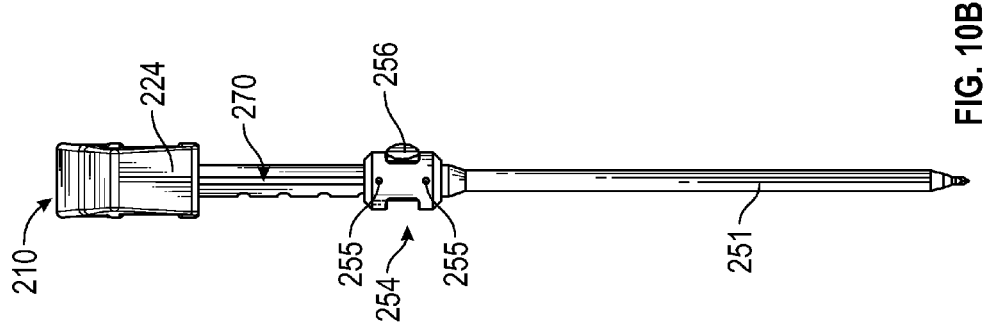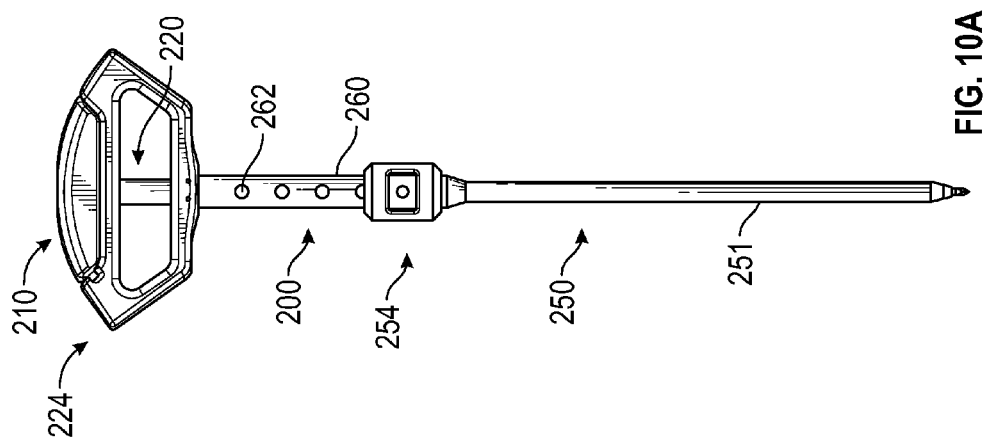

DEPTH CONTROLLED NEEDLE ASSEMBLY

BACKGROUND

Field

The present application relates to orthopedic surgery in general, and more particularly, to needle assemblies having features to control the depth to which the needle is inserted in a target location in a patient.

Description of the Related Art

Needle assemblies, for example, jamshidi type needles, are used for a variety of procedures, for example, for bone marrow biopsies, delivering bone graft and/or other materials to a target location, or to access a target location and form a pilot hole, for example to access a pedicle for delivery of a pedicle screw. In some procedures, there is a risk of damaging nerves near the target anatomical structure. For example, in pedicle screw placement procedures, there is a risk of cracking or otherwise compromising the bone and the pedicle screw contacting the underlying nerves or blood vessels, which can cause pain and/or complications for the patient.

SUMMARY

The present disclosure provides needle assemblies that include depth-stop mechanisms that help inhibit the needle from being driven too far into the target bone. In some embodiments, the needle assemblies include sheaths or sleeves configured to inhibit further advancement of the needle into the target location.

In some embodiments, a needle assembly includes an elongate needle having a sharp tip, a cannula sub-assembly, and a sheath. The cannula sub-assembly includes an elongated shaft having a lumen therethrough, the lumen configured to receive the needle. The sheath has a lumen therethrough. The cannula shaft is disposed in the lumen of the sheath, and the sheath is configured to slide longitudinally relative to the cannula shaft. The sheath is adjustable to one of a plurality of discrete positions relative to the cannula shaft.

In some embodiments, the needle assembly further includes an adjustment mechanism coupled to a proximal portion of the sheath, the adjustment mechanism configured to slide along the cannula sub-assembly and configured to be used to adjust the sheath to one of the plurality of discrete positions relative to the cannula shaft. In some embodiments, the sheath includes a radiopaque marker at or near a distal end of the sheath. In some embodiments, the sheath is made of or includes a radiopaque material.

The needle assembly can further include a hollow attachment member disposed about the cannula shaft, wherein the adjustment mechanism is disposed about and configured to slide along the attachment member and configured to releasably engage the attachment member to adjust the sheath to one of the plurality of discrete positions relative to the cannula. The sheath can be disposed about the attachment member. Alternatively, a proximal portion of the sheath can slide within the attachment member. The cannula sub-assembly can further include a handle coupled to a proximal end of the cannula shaft, and the attachment member can be integrally formed with the handle. In some embodiments, at least a portion of the attachment member has a non-circular cross-section and at least a proximal portion of the lumen of the sheath has a corresponding non-circular cross-section. The cross-sections of at least a portion of the attachment member and at least a proximal portion of the lumen of the sheath can be plus-sign shaped. In some embodiments, a distal end of the attachment member includes a grapple hook configured to inhibit the sheath from sliding distally off of the attachment member.

In some embodiments, a rear side of the attachment member includes a series of longitudinally spaced holes and the adjustment mechanism includes a spring-loaded selector button. The selector button can include a body portion having a central opening configured to receive the attachment member, a button disposed on a front side of the body portion, a spring disposed within the body portion, and a spring retainer on a rear side of the body portion having a forwardly-projecting pin sized to fit within each of the series of spaced holes. In some embodiments, the body portion is disposed about the attachment member, the button is configured to be depressed to urge the pin out of one of the series of spaced holes so that the adjustment mechanism can be slid along the attachment member, and when the button is released, the spring is configured to bias the pin into one of the series of spaced holes.

In some embodiments, a needle assembly kit includes an elongated needle having a sharp tip, a cannula sub-assembly, and at least two sheaths. The cannula sub-assembly includes an elongated shaft having a lumen therethrough, the lumen of the cannula shaft configured to receive the needle. Each sheath includes a lumen therethrough, and the cannula shaft is configured to be disposed in the lumen of the sheath. Each of the at least two sheaths has a different length.

In some embodiments, the cannula sub-assembly further includes a mount, and each of the sheaths includes a coupling portion at a proximal end of the sheath configured to couple to the mount. The coupling portion can include a recess extending from a proximal end of the coupling portion and configured to receive the mount. The mount can be disposed around the shaft of the cannula sub-assembly. In some such embodiments, the cannula sub-assembly further includes a handle coupled to a proximal end of the cannula shaft and the mount is disposed adjacent and distal to the handle. In some embodiments, at least one of front and back sides of the mount includes a post extending forwardly or rearwardly, respectively, and at least one of front and back sides of the recess includes a keyhole shape, wherein a base of the keyhole is configured to receive the post when the sheath is fully mounted on the cannula sub-assembly. In some embodiments, at least one of the at least two sheaths includes a radiopaque marker at or near a distal end of the sheath. In some embodiments, at least one of the sheaths is made of or includes a radiopaque material.

All of these embodiments are intended to be within the scope of the disclosure herein. These and other embodiments will become readily apparent to those skilled in the art from the following detailed description having reference to the attached figures, the disclosure not being limited to any particular disclosed embodiment(s).

BRIEF DESCRIPTION OF THE DRAWINGS

These and other features, aspects, and advantages of the present disclosure are described with reference to the drawings of certain embodiments, which are intended to schematically illustrate certain embodiments and not to limit the disclosure.

FIGS. 10A-10C illustrate another example embodiment of a target needle assembly with an outer sheath in a first position;

DETAILED DESCRIPTION

Figure 1:
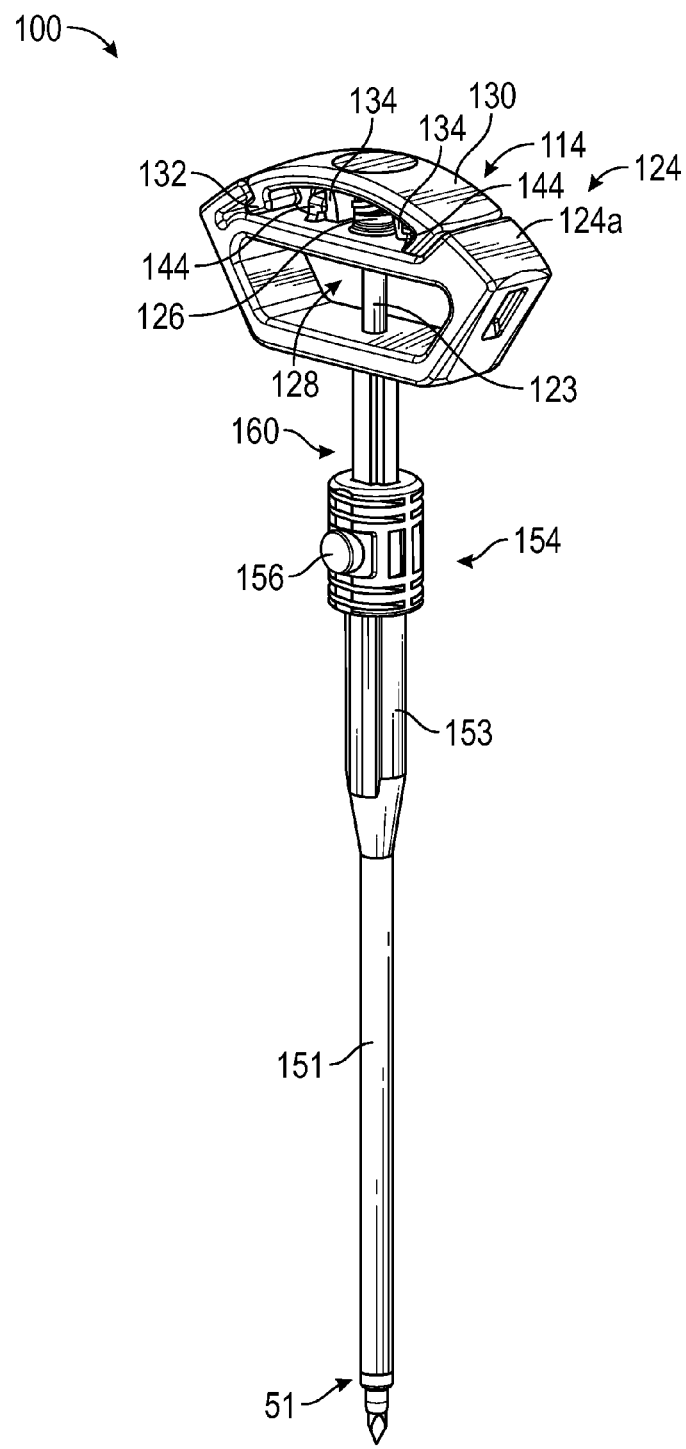
FIG. 1 illustrates a front perspective view of an example embodiment of a target needle assembly.

Although certain embodiments and examples are described below, those of skill in the art will appreciate that the disclosure extends beyond the specifically disclosed embodiments and/or uses and obvious modifications and equivalents thereof. Thus, it is intended that the scope of the disclosure herein disclosed should not be limited by any particular embodiments described below.

Surgeons may use target needle assemblies, such as jamshidi type needles, to access target locations for various procedures. For example, in a pedicle screw placement procedure, a surgeon may use a needle assembly to percutaneously access the target pedicle and form a pilot hole. However, in accessing various target locations, there may be a risk of damaging nearby nerves or blood vessels. For example, if the needle assembly is advanced too far into the bone, the needle assembly, and later implants delivered to the target site, may contact a nerve. As another example, the bone could crack as the pilot hole is being formed, which could expose underlying nerves.

Various embodiments of the present disclosure provide target needle assemblies that include depth-stop mechanisms. A needle assembly as described herein can include an inner shaft having a penetrating tip configured to penetrate into the target bone. The needle assembly can further include an outer sheath disposed around at least a portion of the shaft and configured to limit or inhibit further advancement of the needle into the bone. In some embodiments, the inner shaft is metallic. The outer sheath can be made of any suitable material, such as a plastic or ceramic material. In use, a portion of the shaft that extends distally beyond a distal end of the sheath is able to penetrate into the target bone. The sheath helps inhibit the needle from being advanced too far into the target bone and potentially damaging contacting a nerve, cracking the bone, or causing other adverse effects.

FIGS. 1-8 illustrate an example embodiment of a target needle assembly 100. The needle assembly 100 generally includes a stylet or needle sub-assembly 110, a cannula sub-assembly 120, and a sheath sub-assembly 150. The stylet sub-assembly 110 includes a stylet shaft 112 and a stylet handle 114 coupled to a proximal end of the stylet shaft 112. As shown, the proximal end of the stylet shaft 112 can be coupled to a center of the stylet handle 114. The cannula sub-assembly 120 includes a cannula shaft 122 having a lumen therethrough and a cannula handle 124 coupled to a proximal end of the cannula shaft 122. In the illustrated embodiment, the cannula handle 124 includes a central opening 128. As shown, a portion of the cannula shaft 122, post 123, extends across the central opening 128 to a proximal portion of the cannula handle 124. In some embodiments, various other instruments or components can couple to the post 123. The lumen of the cannula shaft 122 is configured to removably receive the stylet shaft 112. A distal end of the stylet shaft 112 includes a penetrating tip 116 configured to extend beyond a distal end of the cannula shaft 122 when the stylet shaft 112 is inserted into the cannula shaft 122. In use, the penetrating tip 116 is configured to penetrate into bone at the target site. The stylet shaft 112 and/or cannula shaft 122 can be made of a metallic material.

Figure 5:
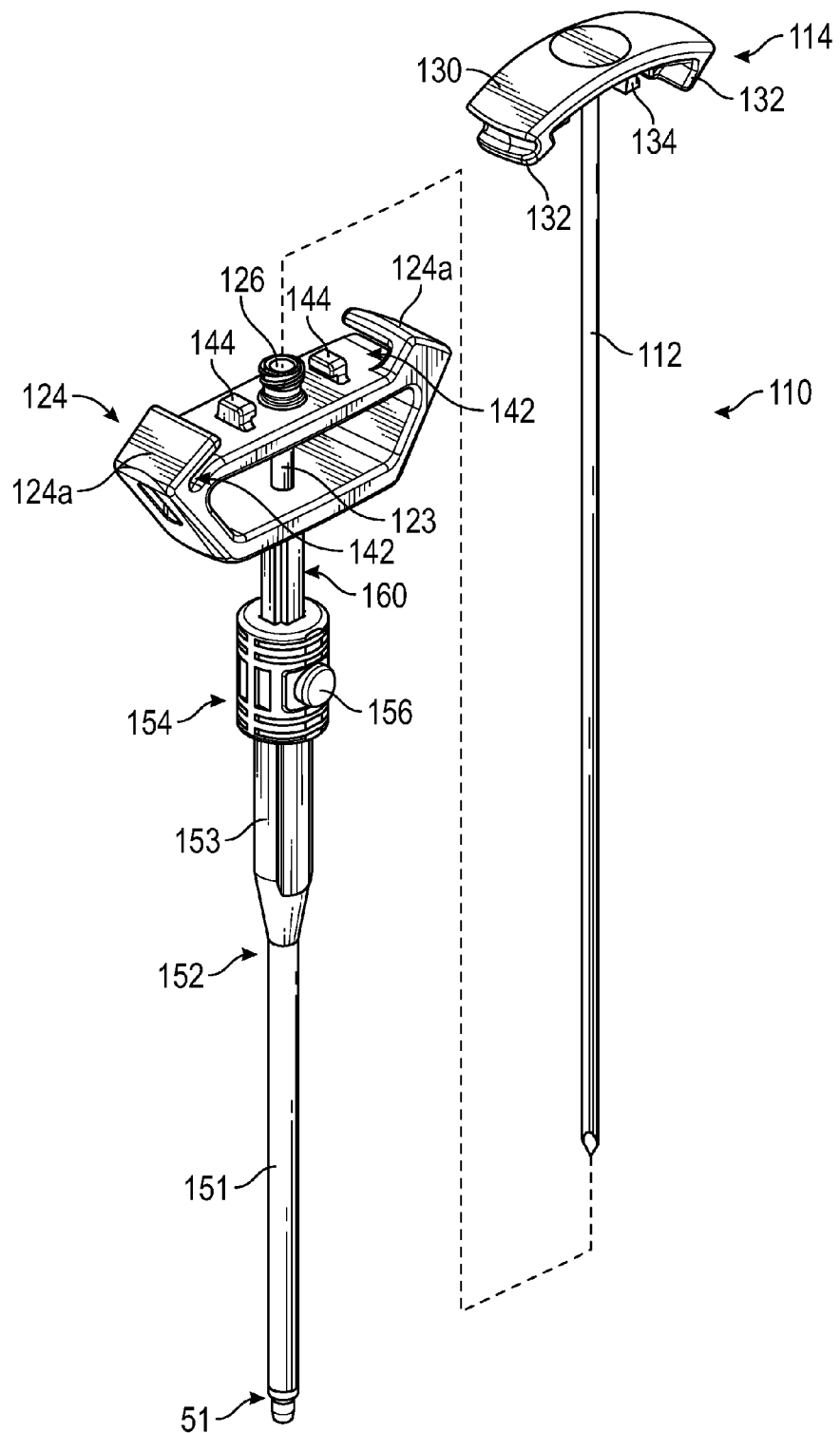
FIG. 5 illustrates an exploded view of the target needle assembly of FIGS. 1-4.

In some embodiments, the stylet handle 114 and cannula handle 124 include features configured to lockingly engage each other to selectively lock the stylet sub-assembly 110 to the cannula sub-assembly 120. For example, in the illustrated embodiment, the stylet handle 114 includes a body portion 130 and two tabs 132, each extending downward and outward from an outer end of the body portion 130. The stylet handle 114 can further include two projections 134, each extending downward from the body portion 130 at a location between the center of the stylet handle 114 and one of the outer ends of the body portion 130. Each of the tabs 132 and projections 134 can be generally L-shaped or elbow shaped. In the illustrated embodiment, the cannula handle 124 includes corresponding recesses 142 configured to receive the tabs 134 and corresponding protrusions 144 configured to engage the projections 134. As shown in FIG. 5, the recesses 142 are formed in proximal side portions 124a of the cannula handle 124 and are open inwardly toward a center of the cannula handle 124. A first recess 142 is open toward the front of the cannula sub-assembly 120, and a second recess 142 is open toward the back of the cannula sub-assembly 120.

To lock the stylet handle 114 to the cannula handle 124, the user can position the stylet handle 114 such that one of the tabs 132 is positioned in front of the first recess 142 and the other tab 132 is positioned behind the second recess 142; the user can then turn the stylet handle 114 relative to the cannula handle 124 to rotate the tabs 132 into the recesses 142. A rear wall of the first recess 142 and a front wall of the second recess 142 can provide stops to prevent or inhibit further rotation of the stylet handle 114 relative to the cannula handle 124 when the tabs 132 are fully received in the recesses 142. In the illustrated embodiment, the stylet handle 114 is rotated clockwise to engage the tabs 132 with the recesses 142 and lock the stylet handle 114 relative to the cannula handle 124. In some embodiments, rotating the stylet handle 114 to position the tabs 132 in the recesses 142 also rotates the projections 134 into engagement with the protrusions 144.

In some embodiments, the cannula handle 124 includes a coupling 126, for example, a luer lock, threaded coupling, or other suitable coupling, that is exposed when the stylet handle 114 is removed from the cannula handle 124. The coupling 126 can be configured to receive, for example, a syringe to aspirate or introduce fluids and/or other materials from or into the target location.

The sheath sub-assembly 150 generally includes a shaft 152, a collar 154, and a lumen extending through the shaft 152 and collar 154. The collar 154 is disposed at a proximal end of the shaft 152. In the illustrated embodiment, the collar 154 is integrally formed with the shaft 152. As shown, an exterior of the collar 154 can be generally cylindrical. In some embodiments, the collar 154 has a non-smooth surface, for example, to allow a user to more easily grip the collar 154. The collar 154 includes an adjustment mechanism configured to be used to adjust the sheath sub-assembly to one of a plurality of discrete positions relative to the cannula as described in greater detail herein. In some embodiments, the adjustment mechanism is configured to be used to adjust the sheath sub-assembly to one of at least three discrete positions relative to the cannula. The sheath sub-assembly 150 can be made of any suitable material, for example, a plastic or ceramic material. In some embodiments, the sheath sub-assembly 150 can be made of a radiopaque material or can include a radiopaque marker or ring 51 at or near a distal end of the shaft 152.

Figure 6:
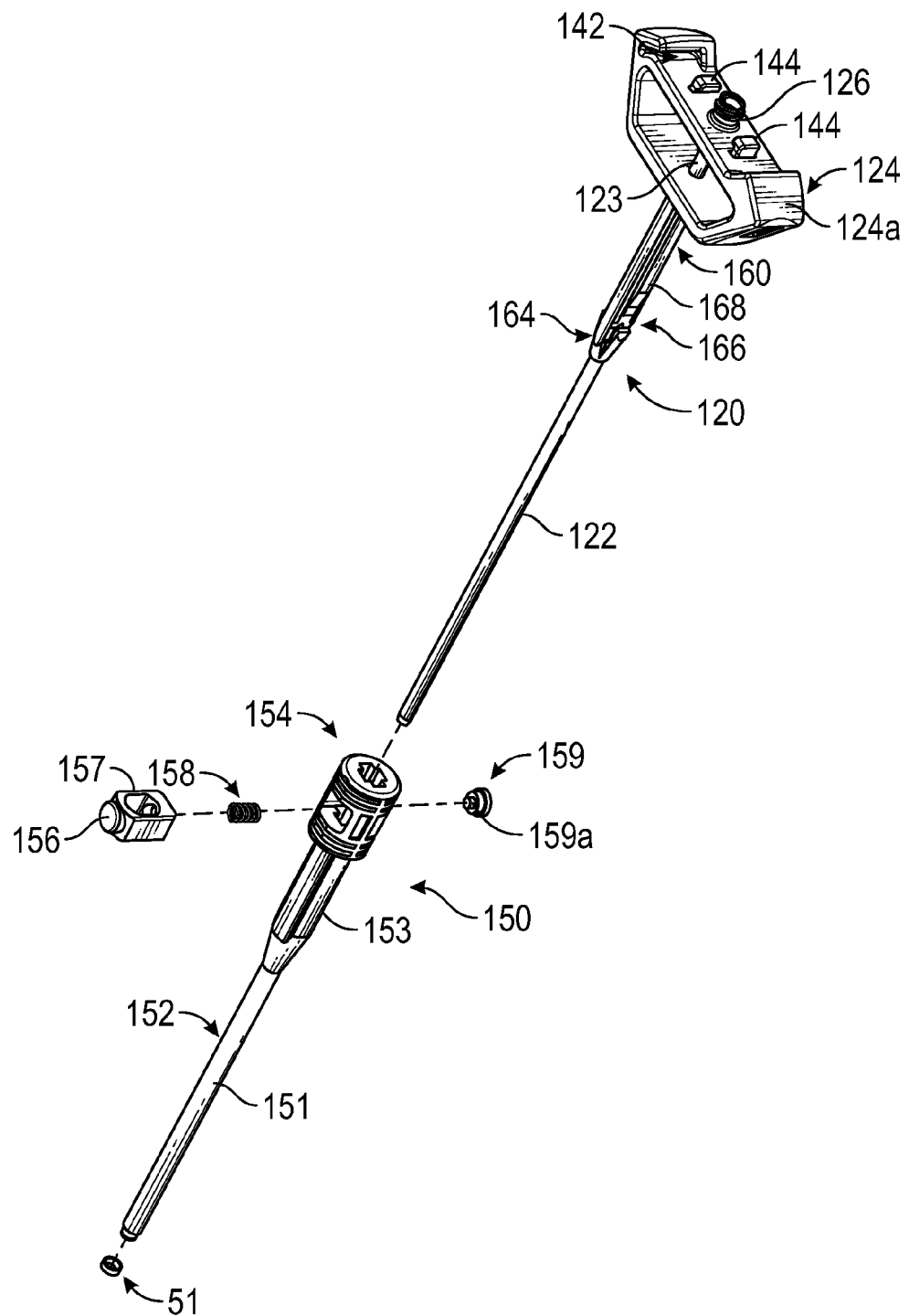
FIG. 6 illustrates an exploded view of a cannula and sheath of the target needle assembly of FIGS. 1-5.

The needle assembly 100, for example, the cannula sub-assembly 120, can further include an attachment member 160 disposed around the cannula shaft 122. The attachment member 160 can generally include a hollow shaft that surrounds a portion of the cannula shaft 122. As shown, the attachment member 160 can surround a portion of the cannula shaft 122 distal to and adjacent or proximate to the cannula handle 124. In some embodiments, the attachment member 160 can have a round, square, rectangular, or other internal cross-sectional shape to correspond to or mate with the portion of the cannula shaft 122 surrounded by the attachment member 160, which may have a round, square, rectangular, or other external cross-sectional shape. The attachment member 160 can have a circular or non-circular external cross-section, for example, a square, rectangular, round, plus-sign or other shaped external cross-section. In some embodiments, the attachment member 160 comprises a cannula. In the illustrated embodiment, the attachment member 160 is integrally formed with and extends distally from the cannula handle 124, as shown in FIG. 6. However, in other embodiments, the attachment member 160 can be separate from the cannula handle 124. The attachment member 160 can be made from, for example, a plastic or ceramic material. The collar 154, and in some cases, a portion of the sheath shaft 152, is disposed about the attachment member 160. In the illustrated embodiment, the sheath shaft 152 includes a distal portion 151 and a proximal portion 153. The distal portion 151 and proximal portion 153 can be integrally formed as shown. In the illustrated embodiment, the proximal portion 153 has a greater diameter than the distal portion 151 to accommodate the attachment member 160.

Figure 2:
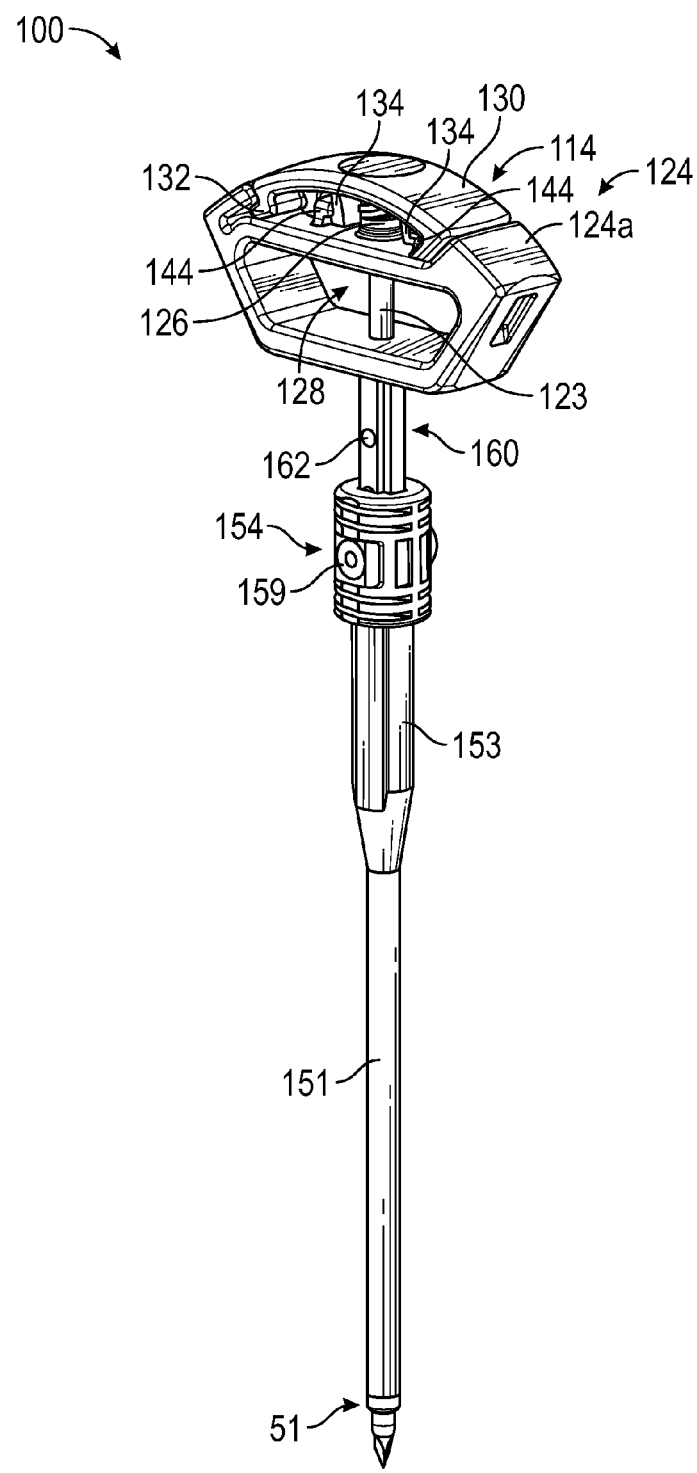
FIG. 2 illustrates a rear perspective view of the target needle assembly of FIG. 1.
Figure 3:
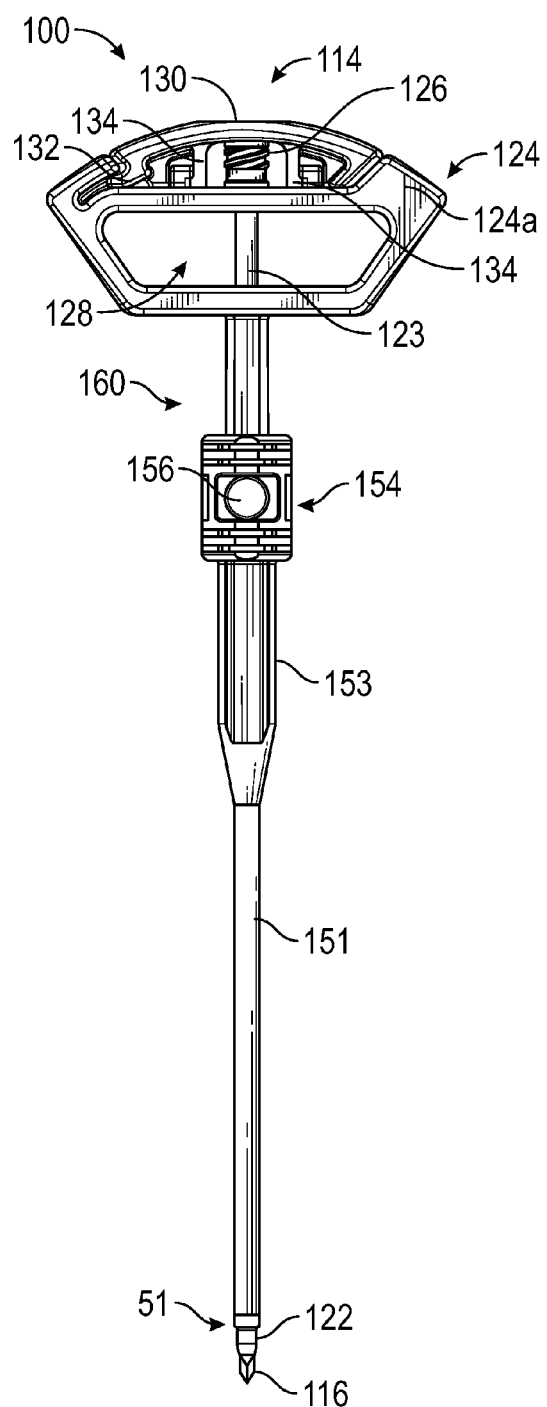
FIG. 3 illustrates a front view of the target needle assembly of FIGS. 1-2.
Figure 4:
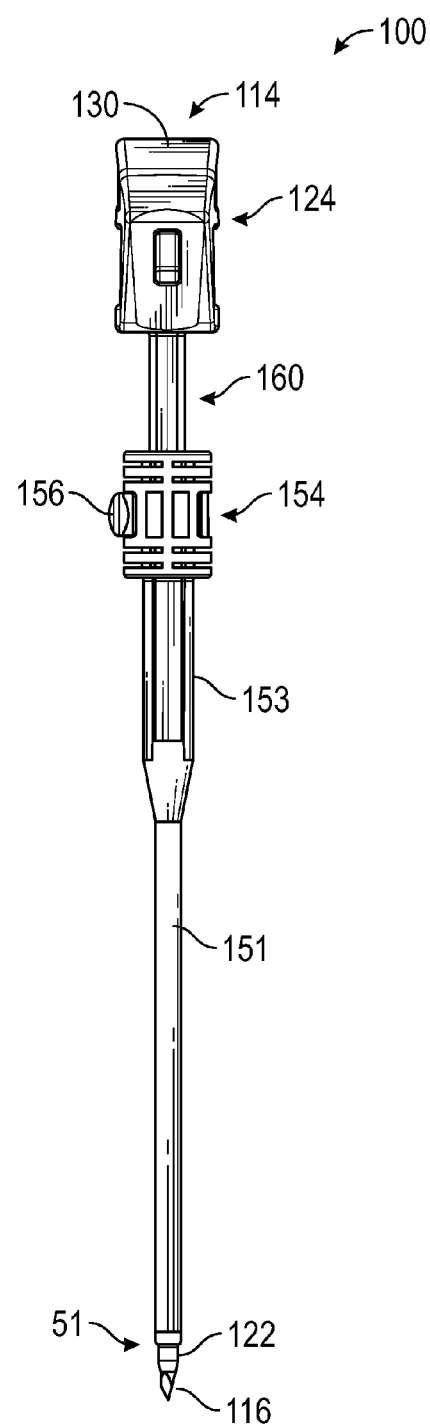
FIG. 4 illustrates a side view of the target needle assembly of FIGS. 1-3.
Figure 8:
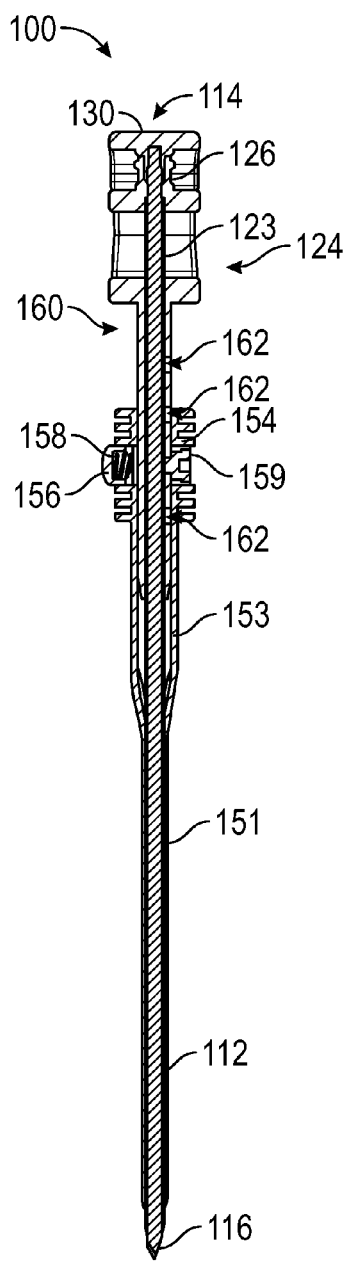
FIG. 8 illustrates a side cross-sectional view of the target needle assembly of FIGS. 1-7.

As shown in FIGS. 2 and 8, a rear side of the attachment member 160 includes a plurality of longitudinally aligned and spaced holes 162. In the illustrated embodiment, the attachment member 160 includes four holes 162, although more or fewer holes are also possible. In the illustrated embodiment, the collar 154 of the sheath sub-assembly 150 includes a spring loaded selector button 156. As shown in the exploded view of FIG. 6 and section view of FIG. 8, the selector button 156 is part of or disposed on a body portion 157. The body portion 157 is disposed in the collar 154. The body portion 157 has a central opening that allows the body portion 157 to receive and be disposed about the attachment member 160. A spring 158 is disposed within the body portion 157 and extends between the button 156 and a front side of the attachment member 160. The body portion 157 also has a rear opening configured to receive a spring retainer 159. The spring retainer 159 is positioned on the back of the collar 154 and operatively coupled to the body portion 157. In some embodiments, the spring retainer 159 is press fit into the body portion 157. The spring retainer 159 includes a forwardly projecting pin 159a sized to fit within the holes 162 of the attachment member 160.

The selector button 156, body portion 157, spring 158, and spring retainer 159 allow the user to adjust the position of the collar 154 and therefore the sheath 150 relative to the attachment member 160 and cannula sub-assembly 120. In a resting state, the pin 159a of the spring retainer 159 is configured to be disposed within one of the holes 162 of the attachment member 160 to lock the position of the collar 154 relative to the attachment member 160. To adjust the sheath sub-assembly 150, the user depresses the button 156, causing the body portion 157 to move rearwardly within the collar 154 and the spring 158 to compress. Because the spring retainer 159 is coupled to the body portion 157, the spring retainer 159 also moves rearwardly, and the pin 159a moves out of the hole 162. The user can then slide the collar 154 and sheath sub-assembly 150 proximally or distally relative to the attachment member 160 and cannula sub-assembly 120. Once the user has positioned the collar 154 at the desired location, he or she releases the button 156. The spring 158 is therefore allowed to expand back to its resting, uncompressed state, which causes the body portion 157 to move forwardly and the spring retainer 159 to move forwardly with the body portion 157. If the pin 159a is aligned with one of the holes 162, the pin 159a will move into the hole 162 to lock the position of the collar 154 relative to the attachment member 160. If the pin 159a is not aligned with one of the holes 162, the collar 154 will not be locked, and the user can slide the collar 154 proximally or distally until the pin 159a engages an adjacent hole 162. The sheath sub-assembly 150 can therefore be adjusted to as many discrete positions as there are holes 162. For example, in the illustrated embodiment, the sheath sub-assembly 150 can be adjusted to four different positions relative to the cannula sub-assembly 120. In other embodiments, the sheath sub-assembly 150 can be adjusted to more or fewer positions relative to the cannula sub-assembly 120. In some embodiments, the sheath sub-assembly 150 can be adjusted to at least three positions relative to the cannula sub-assembly 120.

Figure 7:
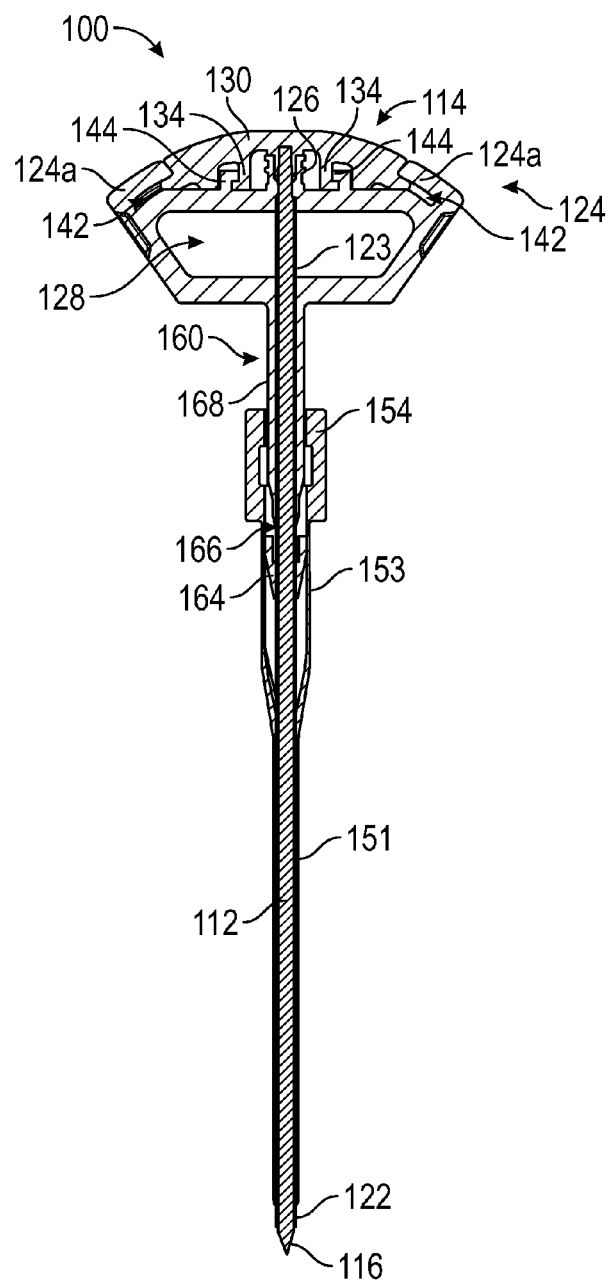
FIG. 7 illustrates a front cross-sectional view of the target needle assembly of FIGS. 1-6.

A distal end of the attachment member 160 can include a grapple hook 164, for example as shown in FIGS. 6-7. The grapple hook 164 can act as a stop to advantageously inhibit the collar 154 from sliding distally off of the attachment member 160. A width of the grapple hook 164 at its widest point is slightly greater than a width of a main body portion 168 of the attachment member 160. The attachment member 160 can include a reduced width portion 166 proximal to the grapple hook 164 and a proximal outward taper from the reduced width portion 166 to the main body portion 168. A width of the central opening of the body portion 157 of the adjustment button is selected to be substantially flush with or to fit snugly to the main body portion 168 of the attachment member 160. The width of the central opening of the body portion 157 is slightly less than the width of the grapple hook 164 at its widest point, as shown in FIG. 7, such that if the collar 154 of the sheath sub-assembly 150 is advanced distally, the body portion 157 will abut the top of the grapple hook 164 and prevent or inhibit the sheath sub-assembly 150 from sliding off of the attachment member 160.

To assemble the needle assembly 100, the sheath sub-assembly 150 is slid proximally onto the cannula sub-assembly 120 and attachment member 160, or the cannula sub-assembly 120 and attachment member 160 are slid distally into the sheath sub-assembly 150. The arms of the grapple hook 164 can flex to compress slightly inward to allow the body portion 157 of the button to slide onto and past the grapple hook 164 and onto the main body portion 168 of the attachment member 160. In some embodiments, the needle assembly 100 can be provided with the sheath sub-assembly 150 preassembled on the cannula sub-assembly 120 and attachment member 160. In other embodiments, the sheath sub-assembly 150 can be assembled onto the cannula sub-assembly 120 and the attachment member 160 by the user, such as a surgeon or other medical personnel. In some such embodiments, sheath sub-assemblies 150 of various lengths can be provided, and the user can select a particular length sheath sub-assembly 150 for use.

In some embodiments, for example as shown in FIGS. 1-8, the lumen extending through the collar 154 and at least a portion of the proximal portion 153 of the sheath shaft 152 has a cross or plus sign-shaped transverse cross-section, and the main body portion 161 of the attachment member 160 has a corresponding cross or plus sign-shaped transverse cross-section. Such non-circular cross-sections can advantageously help keep the collar properly rotationally aligned relative to the attachment member 160 so that the spring retainer is able to engage the holes 162.

As shown, the sheath sub-assembly 150 has a length less than that of the cannula sub-assembly 120. Adjustment of the position of the sheath sub-assembly 150 relative to the cannula sub-assembly 120 adjusts the length of the cannula shaft 122 exposed distal to the sheath sub-assembly 150. The adjustable sheath sub-assembly 150 therefore allows the surgeon to select the length of the exposed portion of the cannula shaft 122 to correspond to the intended depth the pilot hole to be formed in the bone. The exposed portion of the cannula shaft 122 can therefore be limited to the portion of the cannula shaft 122 that will be disposed within the bone. In some embodiments, the distal edge of the sheath sub-assembly 150 can act as a stop to inhibit further advancement of the needle assembly 100 into the bone. This can provide the surgeon with tactile feedback that the needle assembly 100 has reached the desired depth in the bone and reduce the likelihood of advancing the needle assembly 100 beyond a desired depth and potentially contacting or coming too close to an underlying nerve or passing the desired depth for optimal implant positioning. In some embodiments the sheath sub-assembly 150 is made of a radiopaque material or includes a radiopaque marker or ring 51 at or near the distal end, which allows the surgeon to visualize the position of the sheath sub-assembly 150 via imaging techniques. This advantageously allows the surgeon to see where and when the sheath sub-assembly 150 contacts the bone and stop advancing the needle assembly 100. Otherwise, if a surgeon continued to advance the needle assembly 100, for example, by using a mallet or other similar instrument on the stylet handle 114 and/or cannula handle 124, the continued force once the distal end of the sheath sub-assembly 150 contacts the bone could cause the bone and/or sheath sub-assembly 150 to fracture. In any needle assembly according to the present disclosure, including the alternative embodiments shown and described herein, the sheath sub-assembly can be made of a radiopaque material or include a radiopaque marker or ring at or near the distal end. In some embodiments, when the collar 154 is positioned at a distalmost hole 162, the sheath sub-assembly 150 fully covers the distal end of the cannula shaft 122 and/or the penetrating tip 116 of the stylet shaft 112. In other embodiments, when the collar 154 is positioned at the distalmost hole 162, the penetrating tip 116 and/or a portion of the cannula shaft 122 is exposed.

Figure 9:
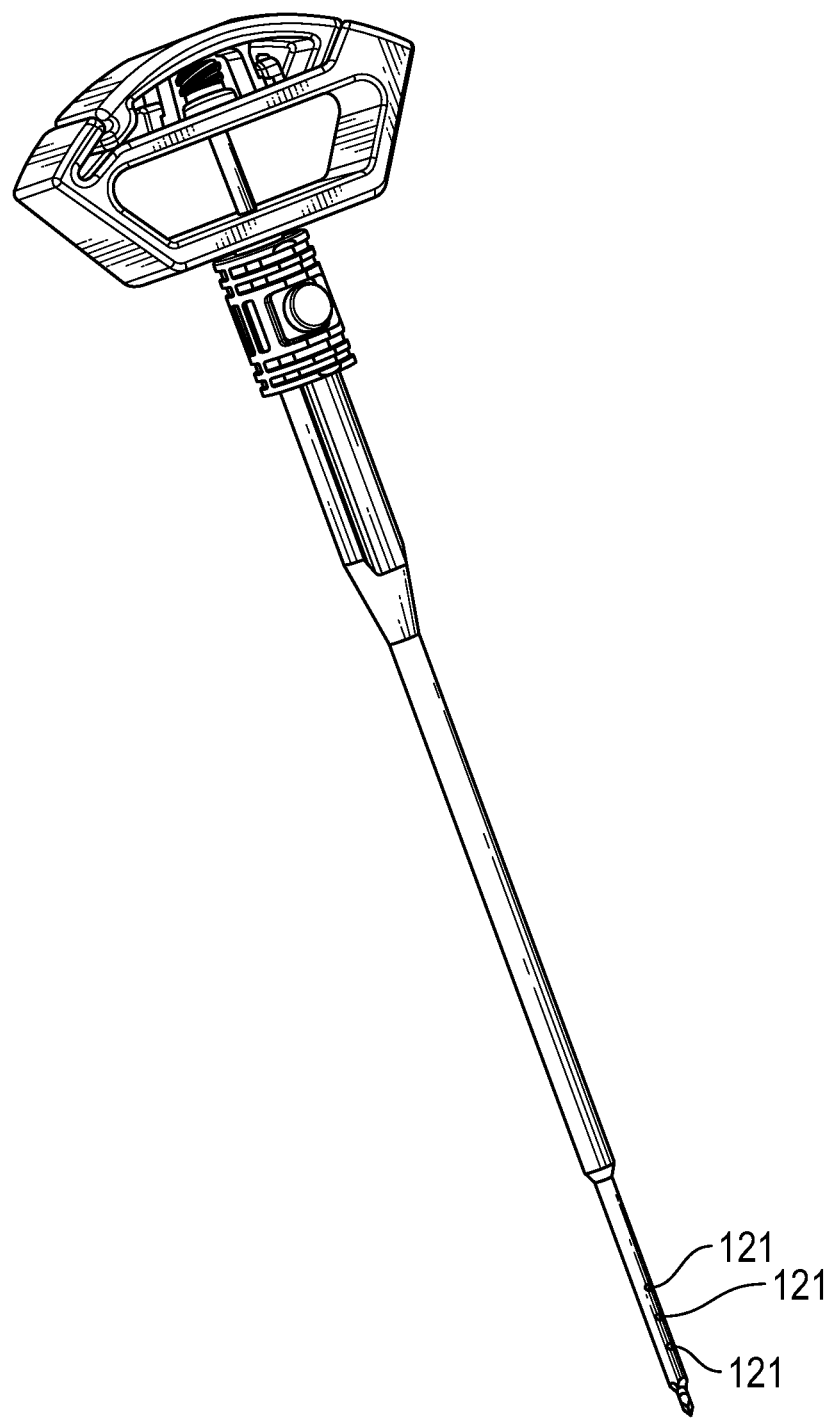
FIG. 9 illustrates an example embodiment of a target needle assembly.

In some embodiments, the collar 154, another portion of the sheath sub-assembly 150, attachment member 160, or cannula sub-assembly 120 can include depth markers or an indication of the length of the exposed portion of the cannula shaft 122 extending from the distal end of the sheath sub-assembly 150 and depth the needle assembly 100 will penetrate into the bone. For example, the attachment member 160 can include markings associated with or corresponding to each hole 162 to indicate the length of the exposed portion of the cannula shaft 122 when the spring retainer pin 159a is positioned in that hole 162. In some embodiments, for example as shown in FIG. 9, the cannula shaft 122 can include depth markings 121 near the distal end of the cannula shaft 122. The depth markings 121 can be spaced at various intervals. For example, in some embodiments, the depth markings 121 are spaced at 5 mm intervals.

In use, once the surgeon identifies the target location, for example, via imaging techniques, the surgeon advances the target needle assembly 100 through skin, muscle, and/or other tissue to the target location, such as a pedicle or other bony anatomical region. The penetrating tip 116 is used to break through the cortical bone and allow the target needle assembly 100 to advance toward the cancellous bone. The surgeon can adjust the position of the sheath sub-assembly 150 relative to the cannula sub-assembly 120 to adjust the length of the exposed portion of the cannula shaft 122 before and/or during the procedure. For example, the surgeon can adjust the sheath sub-assembly 150 such that the length of the exposed portion of the cannula shaft 122 corresponds to the desired depth for the pilot hole to be formed. In some procedures, if the surgeon determines during the procedure that the needle assembly 100 should penetrate to a greater or lesser depth, the surgeon can readjust the position of the sheath sub-assembly 150.

Other attachment and adjustment mechanisms for the sheath sub-assembly are also possible. For example, FIGS. 10A-10F illustrate an alternative embodiment of a target needle assembly 200. Similar to the embodiment of FIGS. 1-8, the target needle assembly 200 includes a stylet sub-assembly 210, cannula sub-assembly 220, sheath sub-assembly 250, collar 254, and attachment member 260 including a series of holes 262. However, in the embodiment illustrated in FIGS. 10A-10F, a proximal portion of the sheath shaft 251 is disposed and moves within the attachment member 260. The attachment member 260 can be integrally formed with or separate from the cannula handle 224.

Figure 10F:
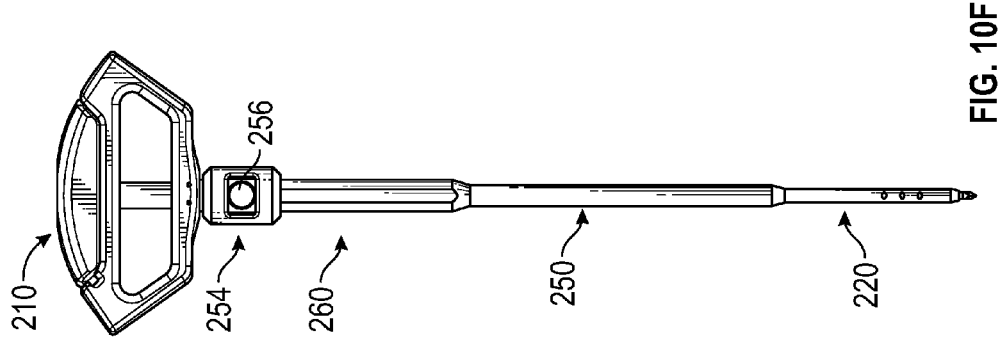
FIGS. 10D-10F illustrate the target needle assembly of FIGS. 10A-10C with the outer sheath in a second position.
Figure 10E:
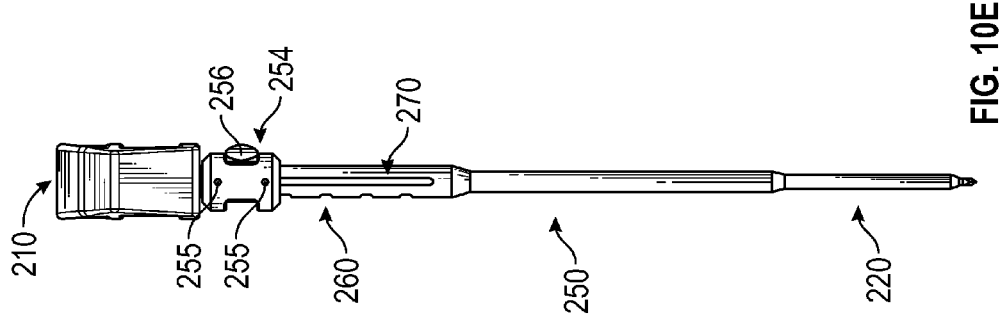
Figure 10D:
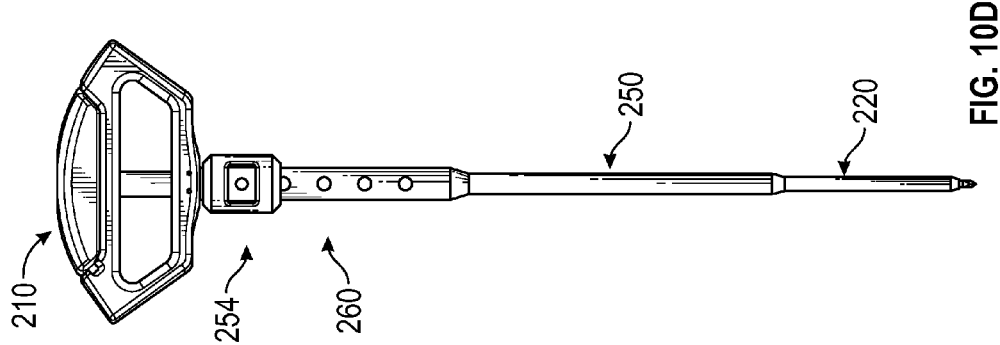
Figures 10G, 10H, 10I:
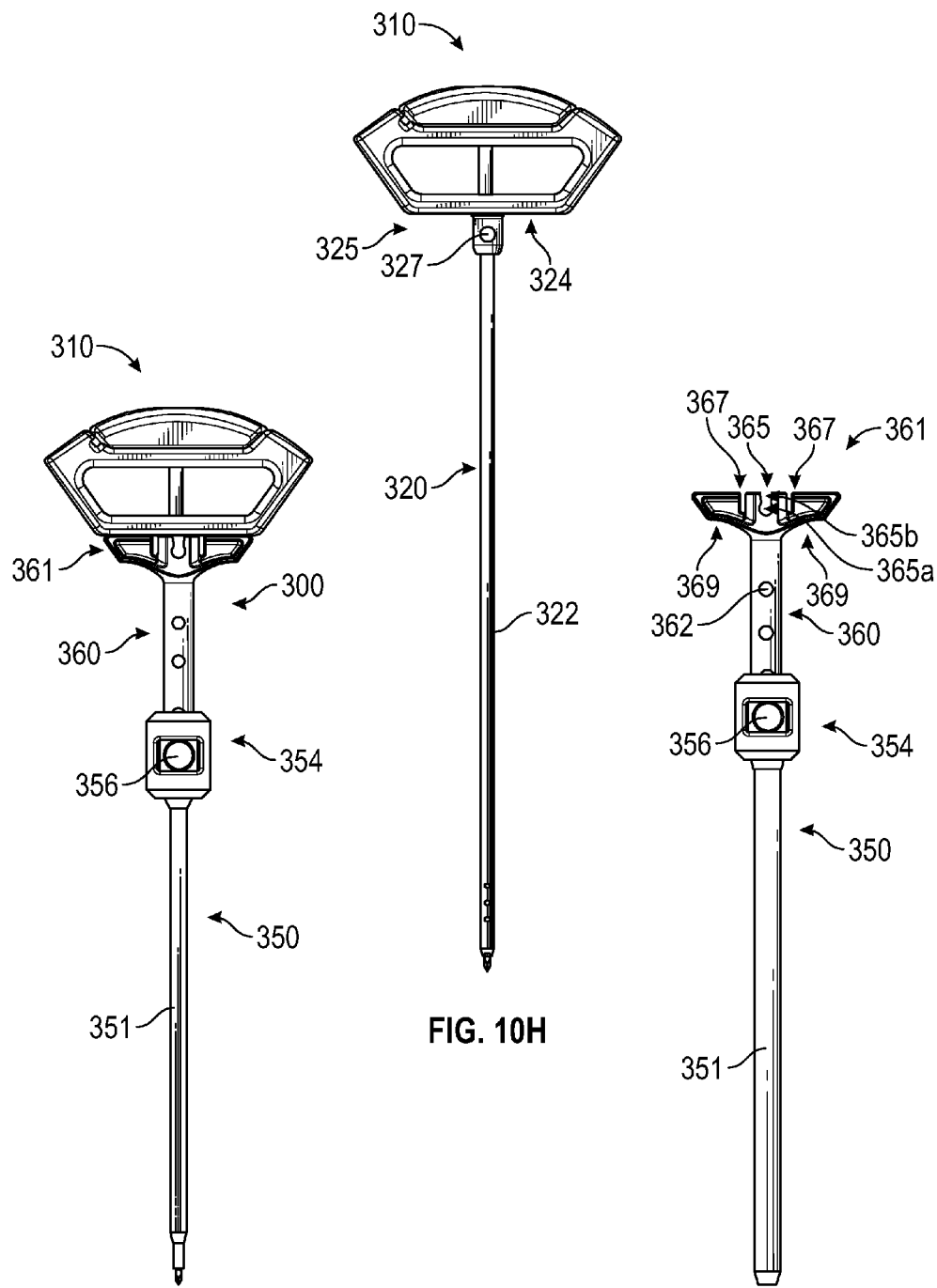
FIGS. 10G-10K illustrate an alternative embodiment of a target needle assembly.
Figure 10J:
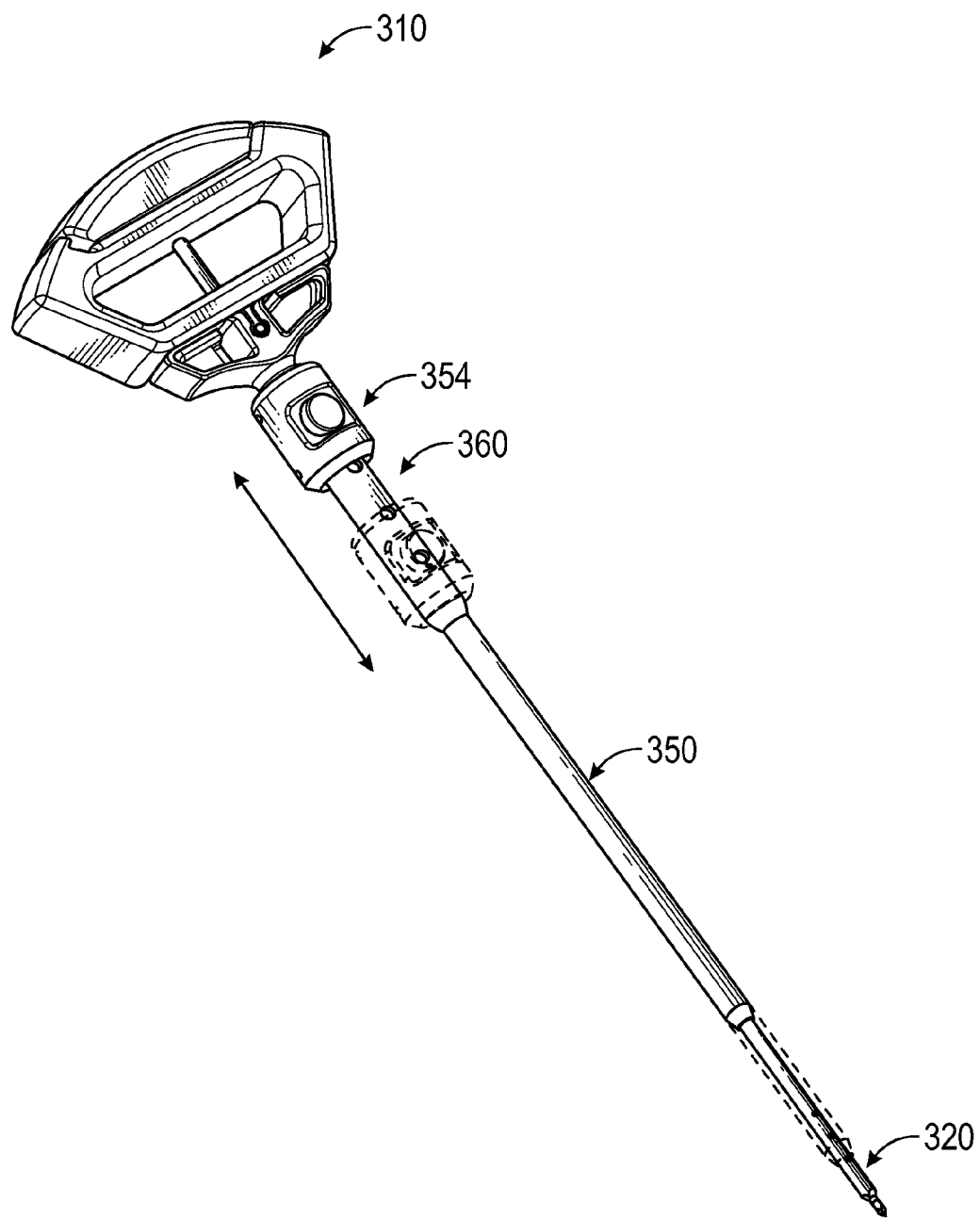
Figure 10K:
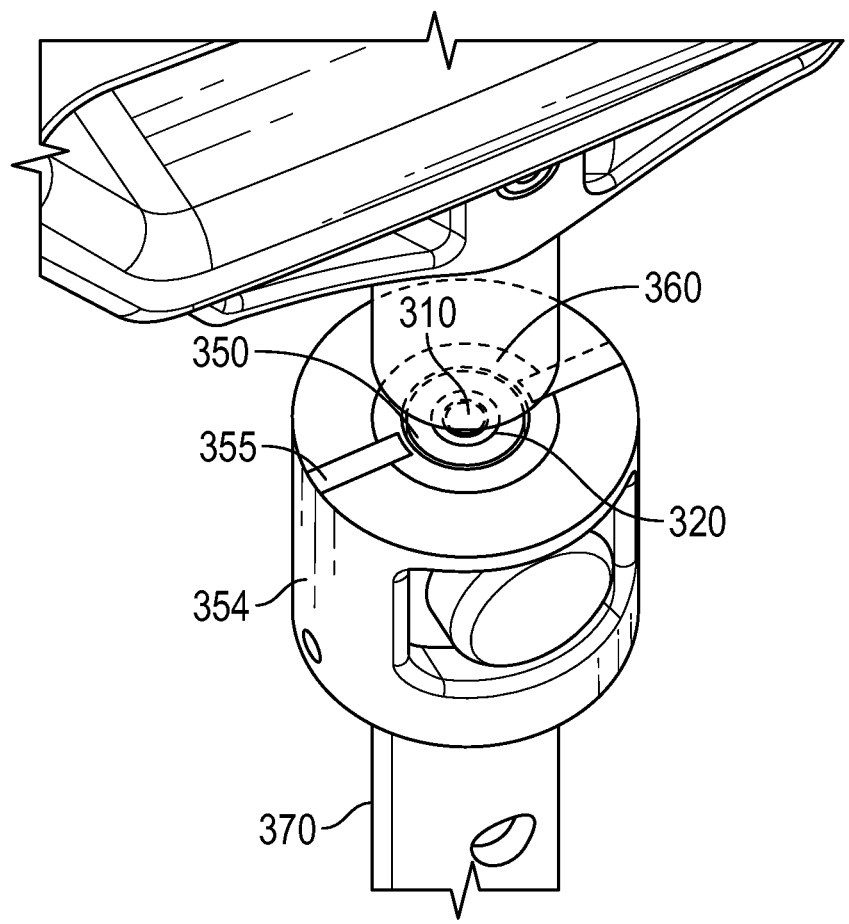

FIGS. 10G-10K illustrate another embodiment of a target needle assembly 300 including a stylet sub-assembly 310, cannula sub-assembly 320, sheath sub-assembly 350, collar 354, and attachment member 360 including a series of holes 362 and in which the sheath shaft 351 is disposed and moves within the attachment member 360. The embodiment of FIGS. 10G-10K is modular. As shown in FIGS. 10H-10I, the attachment member 360 and sheath sub-assembly 350 can be provided separately from the stylet sub-assembly 310 and cannula sub-assembly 320. The attachment member 360 and sheath sub-assembly 350 can be slid proximally onto the cannula sub-assembly 320. The attachment member 360 includes a coupling portion 361 configured to couple to the cannula sub-assembly 320. In the illustrated embodiment, as shown in FIG. 10H, the target needle assembly 300 includes a mount 325 disposed around the cannula shaft 322 adjacent and distal to the cannula handle 324 and fixed to the cannula shaft 322 and/or cannula handle 324. At least one of the front and back sides of the mount 325 can include a post or protrusion 327. A proximal side of the coupling portion 361 of the attachment member 360 includes a recess 365, as shown in FIG. 10I, configured to receive and couple to the mount 325, for example, via a snap fit or friction fit. At least one of the front and back sides of the recess 365 can have a keyhole shape as shown in FIG. 10I. A base 365a of the keyhole is configured to receive the protrusion 327 when the attachment member 360 is fully mounted on the cannula sub-assembly 320, and a narrower neck 365b of the keyhole helps secure the keyhole about the protrusion 327 and secure the coupling portion 361 to the mount 325. The proximal side of the coupling portion 361 can also include a slit 367 on each side of the recess 365 to allow portions of the coupling portion 361 on either side of the recess 365 to flex outwardly so that the neck 365b of the keyhole can be pushed around and past the protrusion 327 as the attachment member 360 is slid onto the cannula sub-assembly 320. In some embodiments, a distal side of the coupling portion 361 has a contoured surface or grips 369, which can advantageously allow the surgeon to more easily hold and manipulate the assembled needle assembly 300.

A modular configuration can advantageously allow the surgeon to choose to use the needle assembly with or without the sheath sub-assembly. Other embodiments of target needle assemblies as described herein and according to the present disclosure can also include modular attachment member sub-assemblies and sheath sub-assemblies. However, in other embodiments, the attachment member 360 can be permanently fixed to the cannula sub-assembly 320.

The target needle assemblies 200, 300 shown in FIGS. 10A-10K include collars 254, 354 including selector buttons 256, 356 to allow for adjustment of the sheath sub-assembly 250, 350 relative to the attachment member 260, 360. As shown in the transverse cross-sectional view of FIG. 10K, the attachment member 360 includes a longitudinal groove 370 extending on each side of the attachment member 360. The collar 354 includes at least one pin 355 extending from each side of the collar 354 into one of the grooves 370. The corresponding pins 355 and grooves 370 help prevent or inhibit rotation of the collar 354 and sheath sub-assembly 350 relative to the attachment member 360. The grooves 370 can also end proximal to a distal end of the attachment member 360 to provide a stop for the pins 355 and prevent or inhibit the collar 354 from disengaging from the attachment member 360. Similarly, in the target needle assembly 200 shown in FIGS. 10A-10F, the collar 254 includes pins 255 extending into longitudinal grooves 270 to help prevent or inhibit rotation of the collar 254 and sheath sub-assembly 250 relative to the attachment member 260.

Figures 11A, 11B:
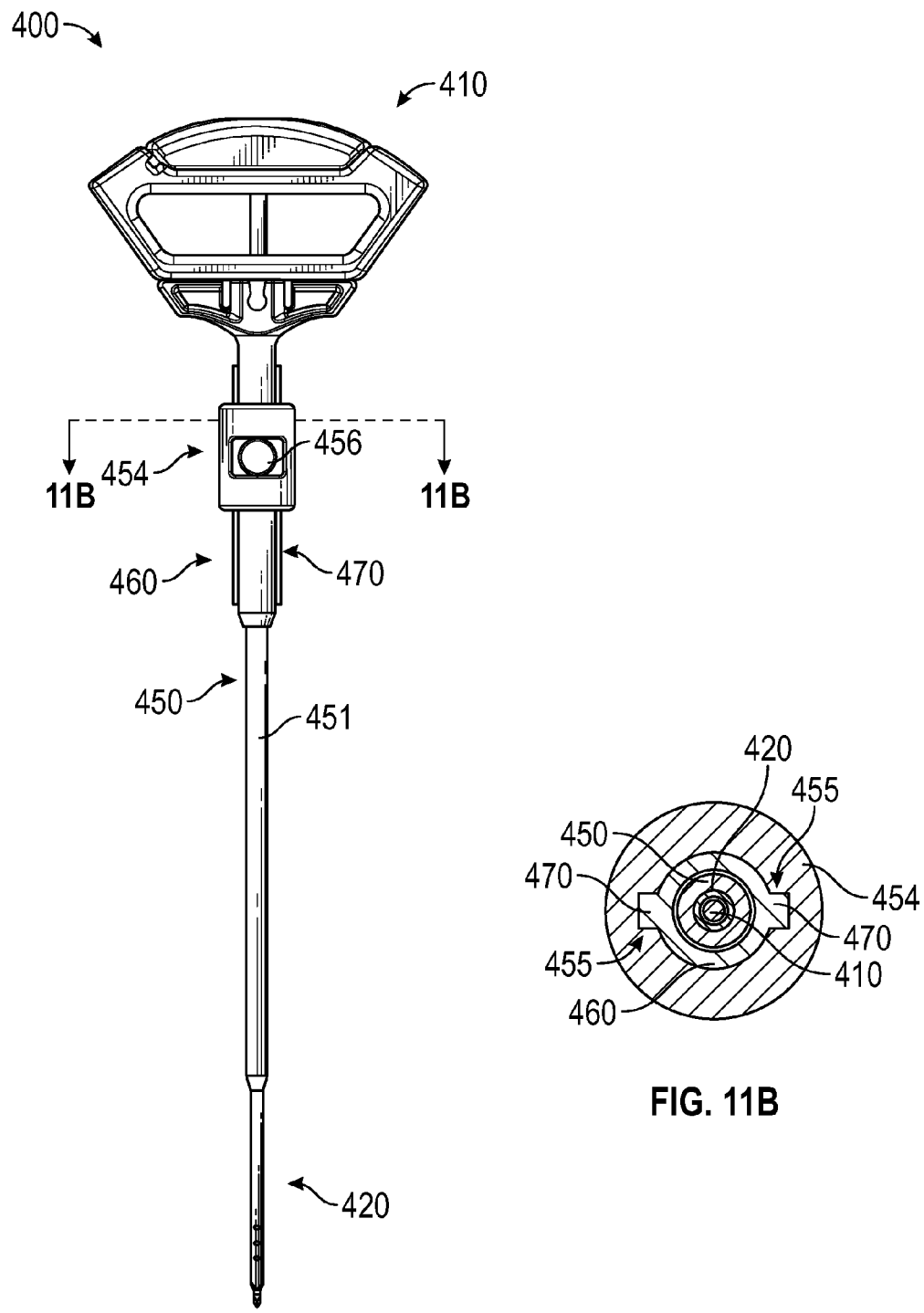
FIGS. 11A-11C illustrate another example embodiment of a target needle assembly.
Figure 11C:
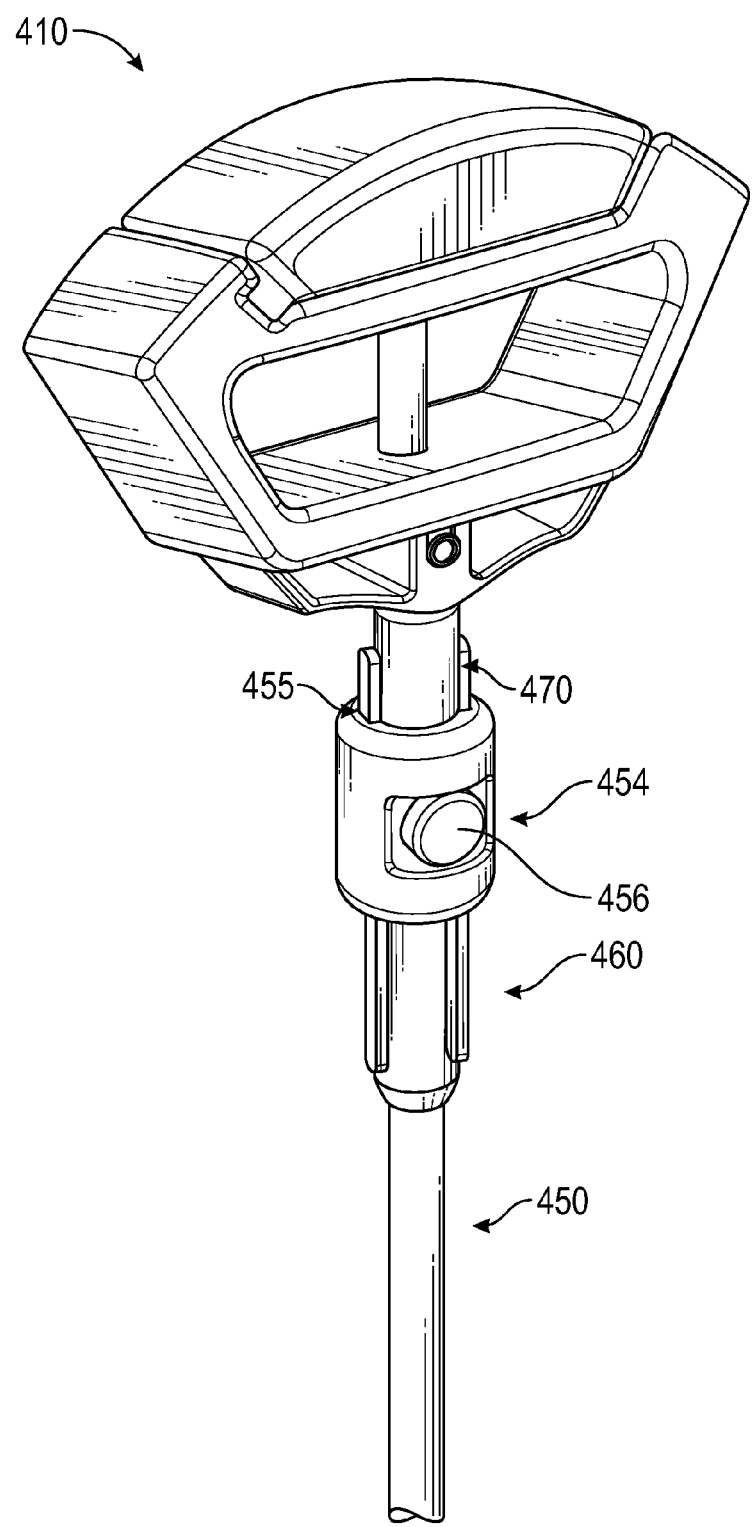

FIGS. 11A-11C illustrate an alternative embodiment of a target needle assembly 400 including a stylet sub-assembly 410, cannula sub-assembly 420, sheath sub-assembly 450, collar 454 including a selector button 456, and attachment member 460. Similar to the embodiments illustrated in FIGS. 10A-10K, a proximal portion of the sheath shaft 451 is disposed and moves within the attachment member 460. However, in target needle assembly 400, the attachment member 460 includes a protrusion 470 on each side configured to act as a track for the collar 454. In inner surface of the collar includes two recesses 455 configured to receive the protrusions 470.

Figure 12C:
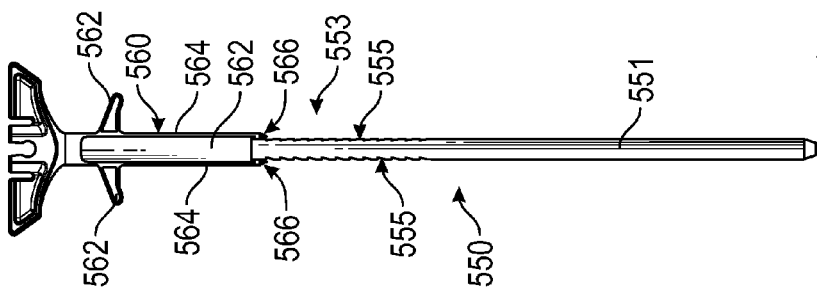
FIGS. 12A-12F illustrate another example embodiment of a target needle assembly.
Figure 12B:
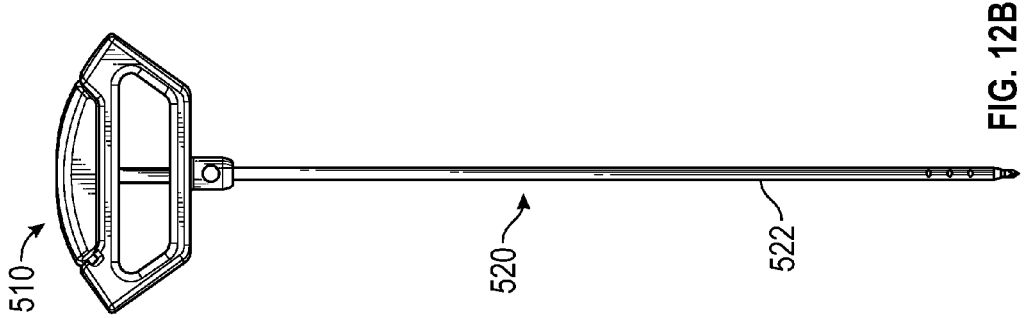
Figure 12A:
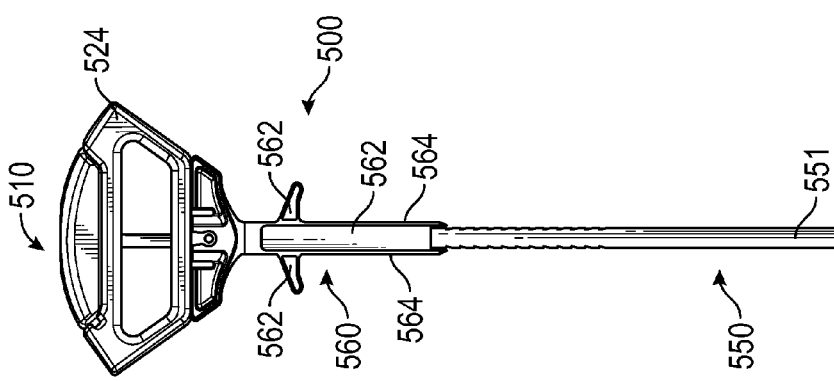

FIGS. 12A-12F illustrate another alternative embodiment of a target needle assembly 500 including a stylet sub-assembly 510, cannula sub-assembly 520, sheath sub-assembly 550, and attachment member 560. A proximal portion of the sheath shaft 551 is disposed and moves within the attachment member 560 via a ratcheting mechanism. As shown in FIGS. 12B and 12C, a proximal portion 553 of the sheath shaft 551 includes a series of notches 555 on each lateral side of the sheath shaft 551. The attachment member 560 includes a body portion 562 and an extension 564 extending longitudinally along each lateral side of the body portion 562. A distal end of each extension 564 has a pawl 566. The pawls 566 are configured to be received in one of the notches 555. The length of the exposed portion of the cannula shaft 522 can be increased by pressing the sheath shaft 551 proximally such that the pawls 566 slide distally along the sheath shaft 551 and series of notches 555 to more distal notches 555. The engagement between the pawls 566 and notches 555 inhibits the sheath shaft 551 from being moved distally.

Figure 12F:
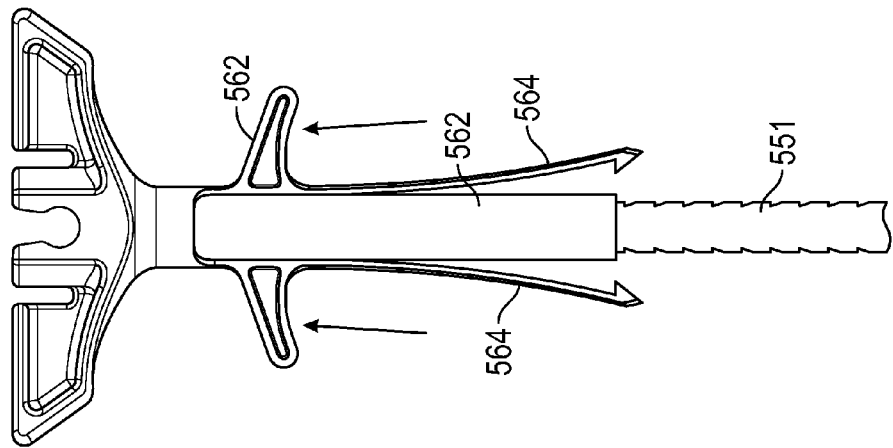
Figure 12E:
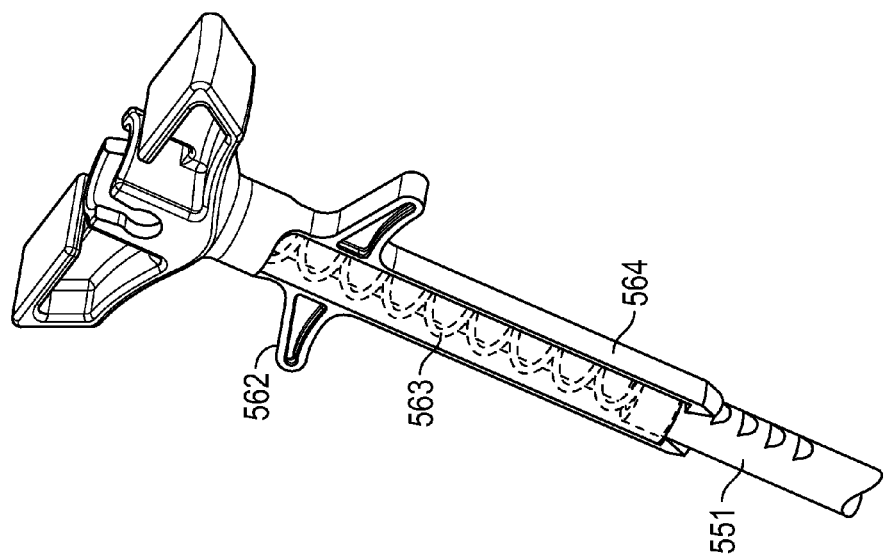
Figure 12D:
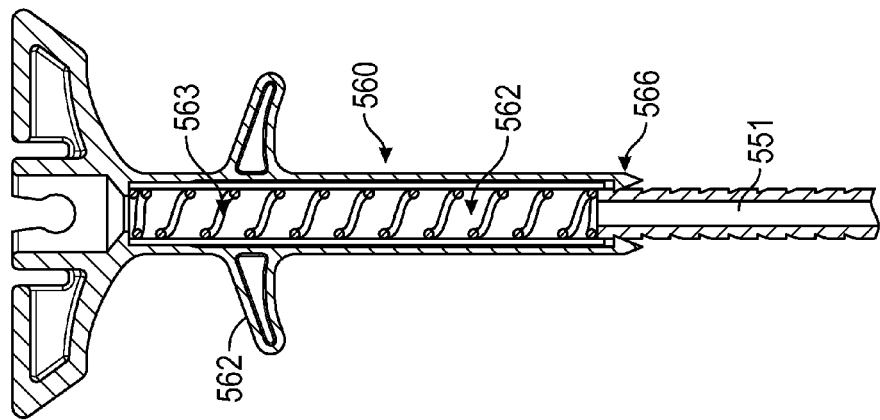

The attachment member 560 can also include tabs 562, which can be positioned such that the tabs 562 are easily gripped by a surgeon when holding the assembled needle assembly 500 via the cannula handle 524. Each of the tabs 562 is integrally formed with or operatively connected to one of the extensions 564. As shown in FIG. 12F, the tabs 562 can be pulled or lifted upward or proximally to cause the extensions 564 to flex outwardly and release the ratcheting mechanism, for example, so that the sheath shaft 551 can be moved distally relative to the attachment member 560. As shown in FIGS. 12D-12E, in some embodiments, the attachment member 560 further includes a spring 563 disposed within the body portion 562. The spring 563 can bias the sheath shaft 551 downwards or distally and provide some resistance to the sheath shaft 551 being inadvertently moved proximally within the attachment member 560, for example, as the needle assembly 500 is advanced into the target location.

Figure 13A:
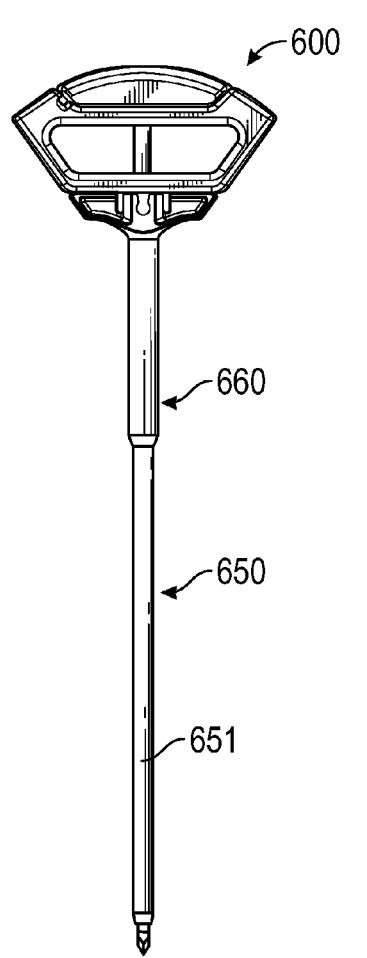
FIGS. 13A-13E illustrate another example embodiment of a target needle assembly.
Figure 13B:
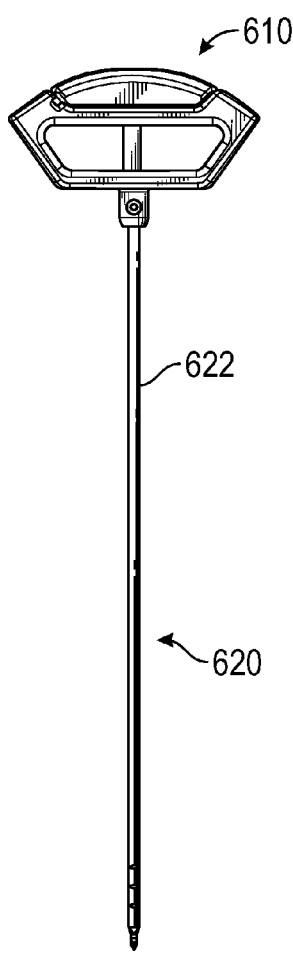
Figure 13C:
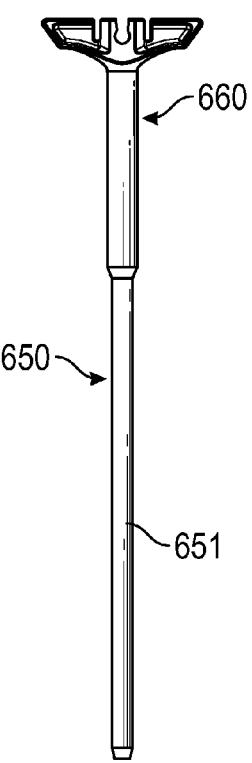
Figure 13E:
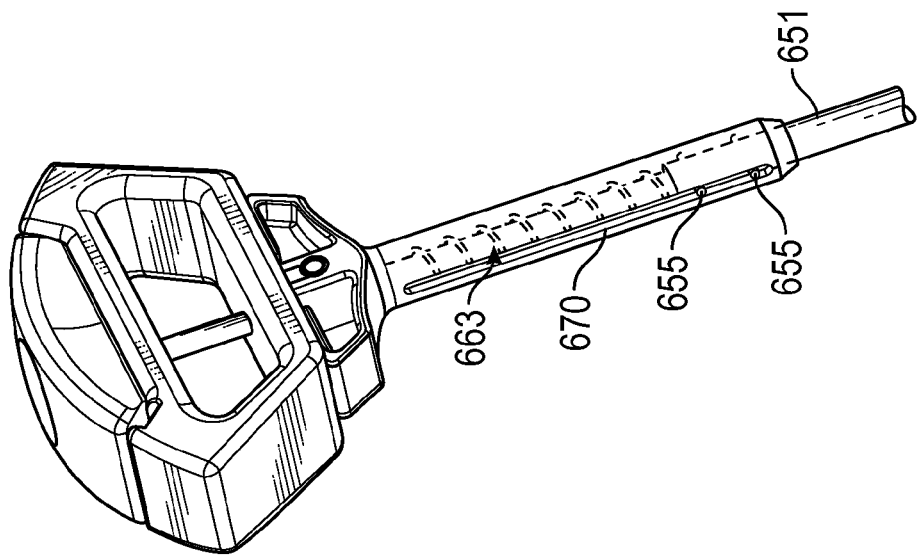
Figure 13D:
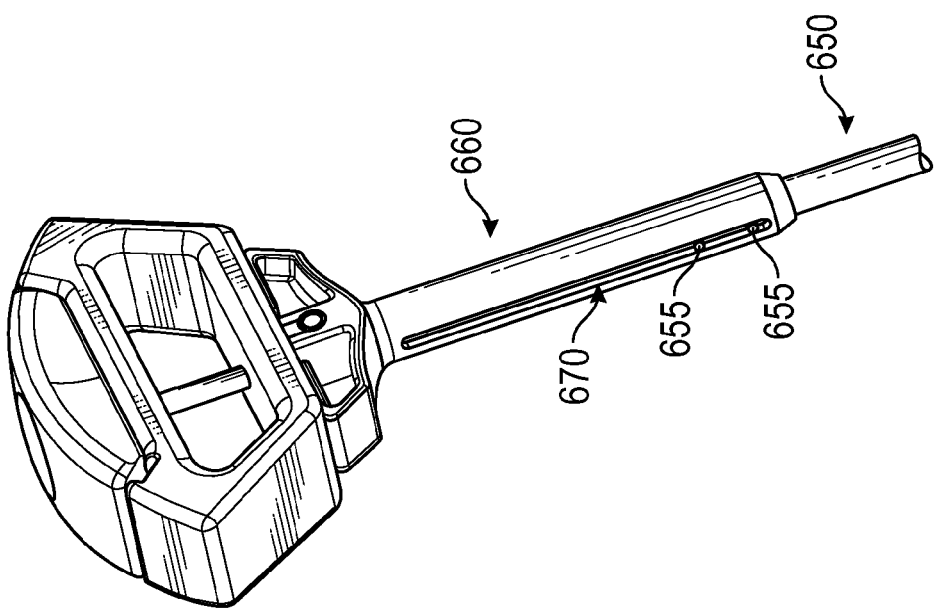
Figure 14A:
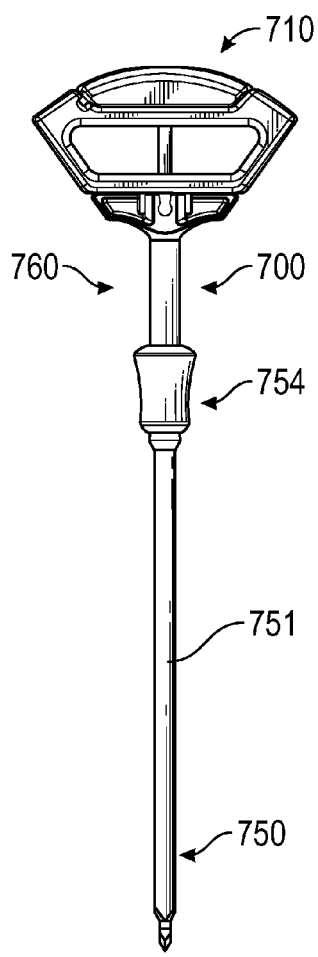
FIGS. 14A-14D illustrate another example embodiment of a target needle assembly.
Figure 14B:
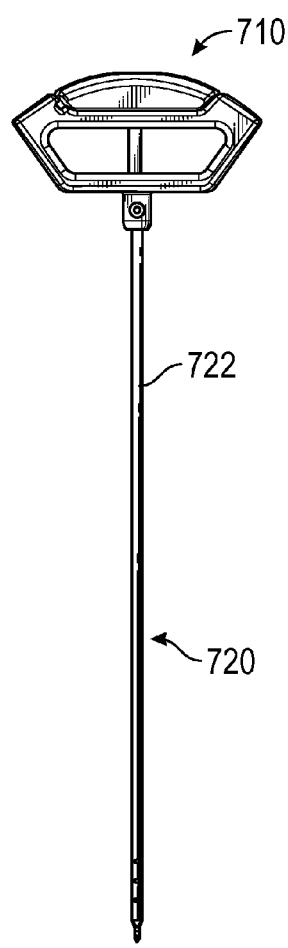
Figure 14C:
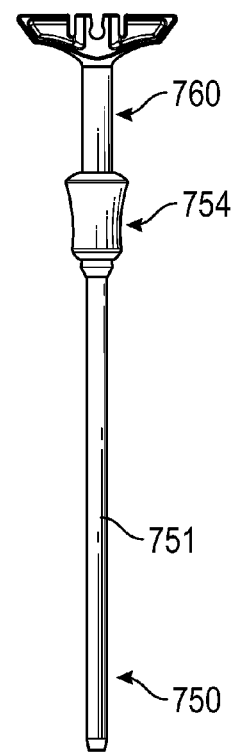
Figure 14D:
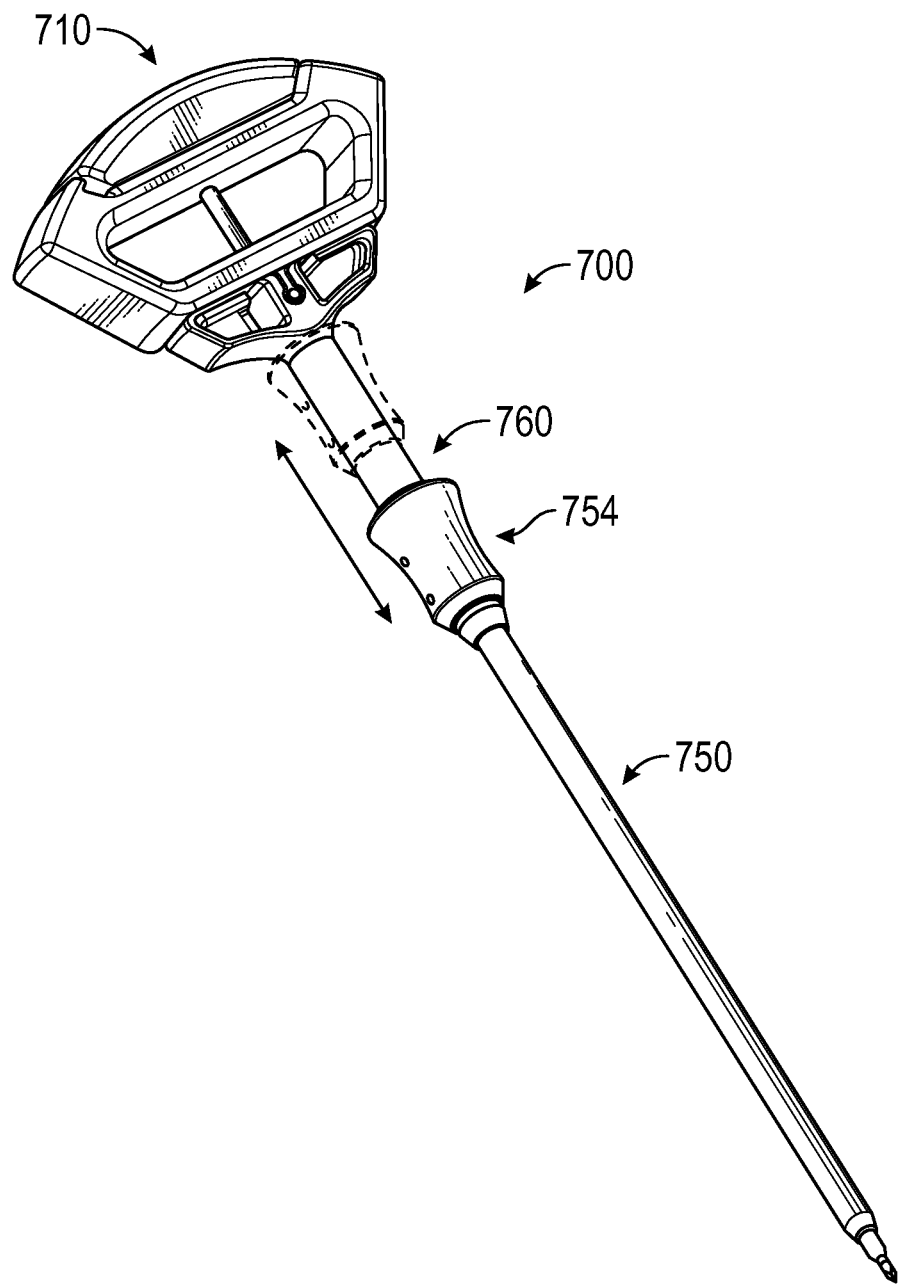

FIGS. 13A-13E illustrate another example embodiment of a target needle assembly 600 including a stylet sub-assembly 610, cannula sub-assembly 620, sheath sub-assembly 650, and attachment member 660 in which a proximal end of the sheath shaft 651 is disposed and moves within the attachment member 660. As shown in FIGS. 13D and 13E, at least one lateral side of the attachment member 660 includes a longitudinal channel 670 running along at least a portion of its length. The sheath sub-assembly 650 includes at least one pin 655 protruding from at least one lateral side of the sheath shaft 651 near the proximal end of the sheath shaft 651. In the illustrated embodiment, the sheath sub-assembly 650 includes two pins 655 that each protrude from both lateral sides of the sheath shaft 651. The pins 655 are received and slide within the channel 670 of the attachment member 660 to help maintain the proper orientation of the sheath sub-assembly 650 relative to the attachment member 660 and/or to inhibit the sheath sub-assembly 650 from disengaging from the attachment member 660. As shown in FIG. 13E, a spring 663 is disposed within the attachment member 660 and applies downward pressure to bias the sheath shaft 651 to a distalmost position in which the cannula shaft 622 is most covered by the sheath shaft 651. The sheath shaft 651 can be moved proximally within the attachment member 660 by simply overcoming the force of the spring 663.

The target needle assembly 700 illustrated in FIGS. 14A-14D also includes a stylet 710, cannula sub-assembly 720, sheath sub-assembly 750, attachment member 760, and spring disposed within the attachment member 760 and is configured such that a proximal end of the sheath shaft 751 is disposed and moves within the attachment member 760. However, the needle assembly 700 includes a collar 754 slideably disposed around the attachment member 760 and operatively coupled to the sheath sub-assembly 750. The internal spring biases the sheath sub-assembly 750 to its distalmost position, but the surgeon can manually move the sheath sub-assembly 750 proximally to expose a greater length of the cannula shaft 722 by sliding the collar 754 proximally along the attachment member 760.

Figure 15:
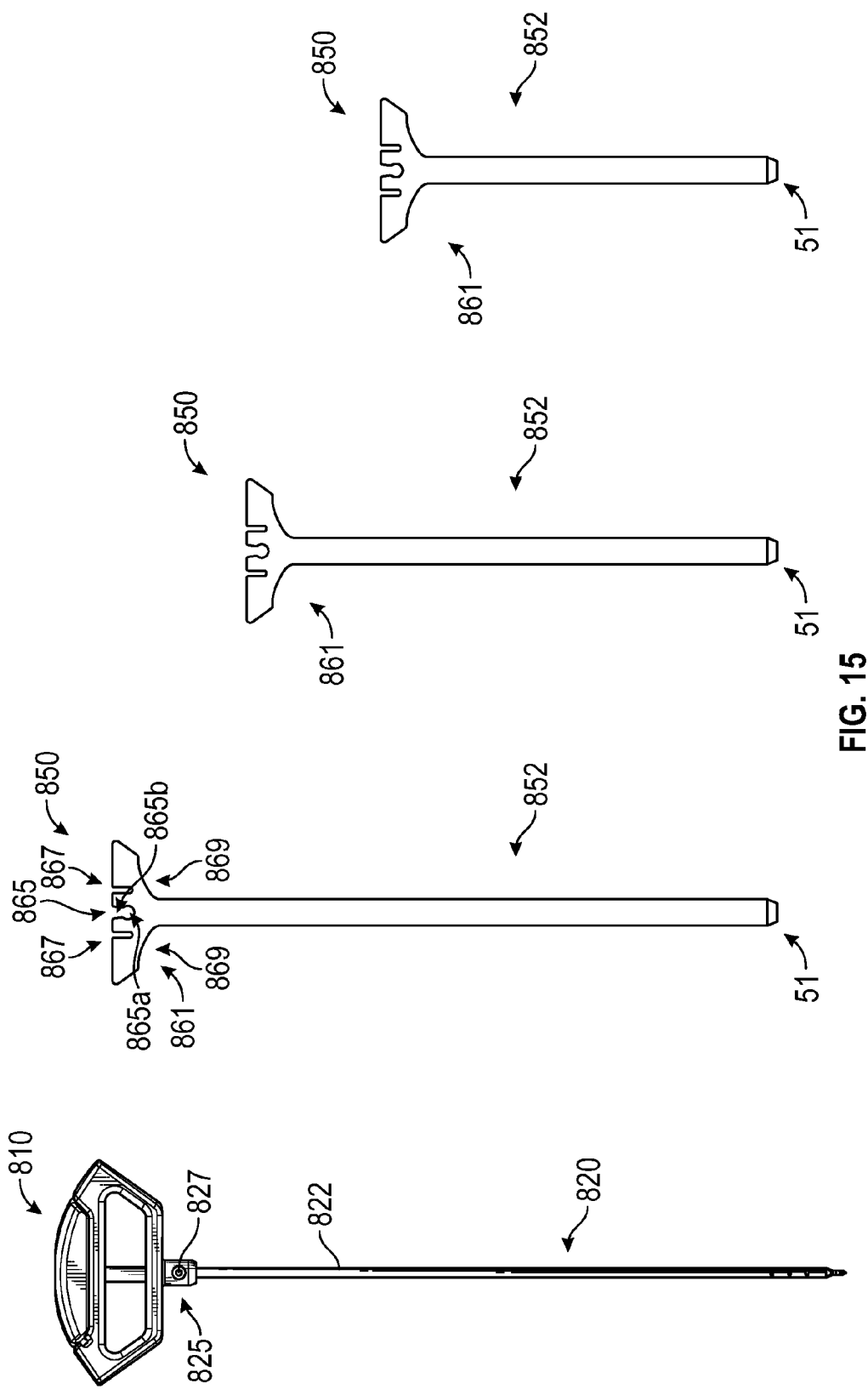
FIG. 15 illustrates an example embodiment of a target needle assembly kit including sheath sub-assemblies having various lengths.

In some embodiments, a target needle assembly includes a stylet, cannula sub-assembly, and sheath sub-assembly similar to embodiments shown and described herein. However, in some embodiments, instead of the sheath sub-assembly being adjustable, the sheath sub-assembly can be configured to have a set length and position relative to the cannula sub-assembly. In some such embodiments, a stylet sub-assembly 810 and cannula sub-assembly 820 can be provided in a kit with two or more sheath sub-assemblies 850 of different lengths, for example as shown in FIG. 15. The surgeon can select the sheath sub-assembly 850 having the appropriate and/or desired length, and attach the selected sheath sub-assembly 850 to the stylet 810 and/or cannula subassembly 820 by sliding the sheath sub-assembly 850 proximally onto the cannula sub-assembly 820. In some embodiments, one or more of the sheath sub-assemblies 850 can be made of a radiopaque material or can include a radiopaque marker or ring 51 at or near a distal end of the shaft 852.

In the illustrated embodiment, each of the sheath sub-assemblies 850 includes a coupling portion 861 configured to couple to the cannula sub-assembly 820. The cannula sub-assembly 820 includes a mount 825 disposed around the cannula shaft 822 adjacent and distal to the cannula handle and fixed to the cannula shaft 822 and/or cannula handle. The coupling portion 861 is configured to couple to the mount 825, for example, via a snap fit or friction fit. The mount 825 and/or coupling portion 861 can be similar to the mount 325 and/or coupling portion 361, respectively, shown in, for example, FIGS. 10G-10I and described herein.

For example, at least one of the front and back sides of the mount 825 can include a post or protrusion 827. A proximal side of the coupling portion 861 of the sheath 850 includes a recess 865 configured to receive and couple to the mount 825, for example, via a snap fit or friction fit. At least one of the front and back sides of the recess 865 can have a keyhole shape. A base 865a of the keyhole is configured to receive the protrusion 827 when the sheath 850 is fully mounted on the cannula sub-assembly 820, and a narrower neck 865b of the keyhole helps secure the keyhole about the protrusion 827 and secure the coupling portion 861 to the mount 825. The proximal side of the coupling portion 861 can also include a slit 867 on each side of the recess 865 to allow portions of the coupling portion 861 on either side of the recess 865 to flex outwardly so that the neck 865b of the keyhole can be pushed around and past the protrusion 827 as the sheath 850 is slid onto the cannula sub-assembly 820. In some embodiments, a distal side of the coupling portion 861 has a contoured surface or grips 869, which can advantageously allow the surgeon to more easily hold and manipulate the assembled needle assembly.

Other mechanisms for coupling the sheath 850 to the cannula sub-assembly 820 are also possible. For example, the sheaths 850 can be coupled to the cannula sub-assembly 820 via a threaded, snap on, clip on, slide on, or other type of connection.

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the principles and features disclosed herein. Various combinations and subcombinations of the various features described herein are possible.

What is claimed is:

1. A needle assembly comprising:
an elongated needle configured to form a hole in bone, the elongated needle having a sharp distal tip and a handle coupled to a proximal end of the needle;
a cannula sub-assembly comprising an elongated shaft having a lumen therethrough, the lumen of the cannula shaft configured to receive the needle, and a handle coupled to a proximal end of the cannula shaft;
a sheath comprising a lumen therethrough, the cannula shaft disposed in the lumen of the sheath and the sheath configured to slide longitudinally relative to the cannula shaft;
a collar coupled to a proximal portion of the sheath, the collar configured to slide along the cannula sub-assembly; and
a hollow attachment member disposed about the cannula shaft, wherein the cross-sections of the at least a portion of the attachment member and the at least a proximal portion of the lumen of the sheath are plus-sign shaped;
wherein the handle of the needle is configured to lockingly engage the handle of the cannula sub-assembly to selectively lock the needle to the cannula sub-assembly and the sheath is adjustable to and configured to be locked at a plurality of discrete positions relative to the cannula shaft when the needle is locked to the cannula sub-assembly to adjust a length of the cannula shaft exposed distal to the sheath, wherein the plurality of discrete positions are positioned such that the length of the cannula shaft exposed distal to the sheath corresponds to a desired depth for the hole formed in bone to allow for control of the depth of the hole formed in bone; and
wherein the collar continuously encircles the attachment member and is configured to slide along the attachment member and releasably engage the attachment member to adjust the sheath to one of the plurality of discrete positions relative to the cannula.

2. The needle assembly of claim 1, wherein the sheath is disposed about the attachment member.

3. The needle assembly of claim 1, wherein the attachment member is integrally formed with the handle coupled to the proximal end of the cannula shaft.

4. The needle assembly of claim 1, wherein a distal end of the attachment member further comprises a grapple hook configured to inhibit the sheath from sliding distally off of the attachment member.

5. The needle assembly of claim 1, wherein the sheath is configured to receive the attachment member.

6. The needle assembly of claim 1, wherein the sheath is configured to slide relative to the cannula handle and cannula shaft.

7. A needle assembly comprising:
an elongated needle configured to form a hole in bone, the elongated needle having a sharp distal tip and a handle coupled to a proximal end of the needle;
a cannula sub-assembly comprising an elongated shaft having a lumen therethrough, the lumen of the cannula shaft configured to receive the needle, and a handle coupled to a proximal end of the cannula shaft;
a sheath comprising a lumen therethrough, the cannula shaft disposed in the lumen of the sheath and the sheath configured to slide longitudinally relative to the cannula shaft;
a collar coupled to a proximal portion of the sheath, the collar configured to slide along the cannula sub-assembly; and
a hollow attachment member disposed about the cannula shaft;
wherein the handle of the needle is configured to lockingly engage the handle of the cannula sub-assembly to selectively lock the needle to the cannula sub-assembly and the sheath is adjustable to and configured to be locked at a plurality of discrete positions relative to the cannula shaft when the needle is locked to the cannula sub-assembly to adjust a length of the cannula shaft exposed distal to the sheath, wherein the plurality of discrete positions are positioned such that the length of the cannula shaft exposed distal to the sheath corresponds to a desired depth for the hole formed in bone to allow for control of the depth of the hole formed in bone;
wherein the collar continuously encircles the attachment member and is configured to slide along the attachment member and releasably engage the attachment member to adjust the sheath to one of the plurality of discrete positions relative to the cannula;
wherein a rear side of the attachment member comprises a series of longitudinally spaced holes and the collar comprises a spring-loaded selector button, the selector button comprising a body portion having a central opening configured to receive the attachment member, a button disposed on a front side of the body portion, a spring disposed within the body portion, and a spring retainer on a rear side of the body portion having a forwardly-projecting pin sized to fit within each of the series of spaced holes, wherein the body portion is disposed about the attachment member, the button is configured to be depressed to urge the pin out of one of the series of spaced holes so that the collar can be slid along the attachment member, and when the button is released, the spring is configured to bias the pin into one of the series of spaced holes.

8. The needle assembly of claim 1, wherein the sheath further comprises a radiopaque marker at or near a distal end of the sheath.

9. The needle assembly of claim 1, wherein the sheath comprises a radiopaque material.

\* \* \* \* \*

UNITED STATES PATENT AND TRADEMARK OFFICE
CERTIFICATE OF CORRECTION

PATENT NO.         : 9,681,889 B1
APPLICATION NO.    : 14/734988
DATED              : June 20, 2017
INVENTOR(S)        : Travis Greenhalgh and Ryan Lewis Page 1 of 1

It is certified that error appears in the above-identified patent and that said Letters Patent is hereby corrected as shown below:

In the Claims

Claim 1, in Column 12, Line 33, before the word at, delete "the"; in Column 12, Line 34, before the word at, delete "the".

Signed and Sealed this
Twenty-ninth Day of June, 2021

Drew Hirshfeld
*Performing the Functions and Duties of the*
*Under Secretary of Commerce for Intellectual Property and*
*Director of the United States Patent and Trademark Office*